United States Patent
Green et al.

(10) Patent No.: US 10,758,487 B2
(45) Date of Patent: Sep. 1, 2020

(54) ARTIFICIAL ANTIGEN PRESENTING CELLS HAVING A DEFINED AND DYNAMIC SHAPE

(71) Applicant: THE JOHNS HOPKINS UNIVERSITY, Baltimore, MD (US)

(72) Inventors: Jordan J. Green, Nottingham, MD (US); Joel C. Sunshine, Pikesville, MD (US); Karlo Perica, Baltimore, MD (US); Jonathan Schneck, Silver Spring, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 0 days.

(21) Appl. No.: 14/363,955

(22) PCT Filed: Dec. 10, 2012

(86) PCT No.: PCT/US2012/068759
§ 371 (c)(1),
(2) Date: Jun. 9, 2014

(87) PCT Pub. No.: WO2013/086500
PCT Pub. Date: Jun. 13, 2013

(65) Prior Publication Data
US 2014/0370099 A1    Dec. 18, 2014

Related U.S. Application Data

(60) Provisional application No. 61/568,751, filed on Dec. 9, 2011.

(51) Int. Cl.
| | | |
|---|---|---|
| *A61K 39/44* | (2006.01) | |
| *A61K 9/16* | (2006.01) | |
| *B29B 9/12* | (2006.01) | |
| *A61K 39/00* | (2006.01) | |
| *A61K 39/002* | (2006.01) | |
| *A61K 39/02* | (2006.01) | |
| *A61K 39/12* | (2006.01) | |

(52) U.S. Cl.
CPC ............ *A61K 9/16* (2013.01); *A61K 39/0001* (2013.01); *A61K 39/0002* (2013.01); *A61K 39/002* (2013.01); *A61K 39/0011* (2013.01); *A61K 39/02* (2013.01); *A61K 39/12* (2013.01); *B29B 9/12* (2013.01); *A61K 2039/5154* (2013.01); *A61K 2039/55555* (2013.01); *B29B 2009/125* (2013.01)

(58) Field of Classification Search
None
See application file for complete search history.

(56) References Cited

U.S. PATENT DOCUMENTS

| | | |
|---|---|---|
| 4,822,534 A | 4/1989 | Lencki |
| 5,259,097 A | 11/1993 | Aihara et al. |
| 6,362,001 B1 | 3/2002 | Cai et al. |
| 7,713,739 B1 | 5/2010 | Donnelly et al. |
| 7,855,074 B2 | 12/2010 | Warren et al. |
| 2002/0146828 A1 | 10/2002 | Hural |
| 2004/0005352 A1 | 1/2004 | Lopez |
| 2004/0115216 A1 | 6/2004 | Schneck et al. |
| 2005/0244505 A1 | 11/2005 | Higbee |
| 2006/0154234 A1* | 7/2006 | Winther .................. G01N 1/36 435/4 |
| 2010/0028450 A1 | 2/2010 | Vasu |
| 2011/0014217 A1* | 1/2011 | Fahmy ............... A61K 38/1709 424/184.1 |
| 2011/0263920 A1* | 10/2011 | Bourke, Jr. .......... A61K 41/008 600/1 |
| 2011/0300168 A1 | 12/2011 | Schneck et al. |
| 2013/0202548 A1* | 8/2013 | Rowan ............. A61K 47/48192 424/78.17 |

FOREIGN PATENT DOCUMENTS

| | | |
|---|---|---|
| WO | 2002056908 A2 | 7/2002 |
| WO | 2009/117616 A2 | 9/2009 |

OTHER PUBLICATIONS

Zheng et al, Structural signatures of dynamic heterogeneities in monolayers of colloidal ellipsoids, Nature Communications, 2014, pp. 1-12.*
Mahapatro and Singh, Biodegradable nanoparticles are excellent vehicle for site directed in-vivo delivery of drugs and vaccines, Journal of Nanobiotechnology 2011, pp. 1-11.*
Morachis et al, Physical and Chemical Strategies for Therapeutic Delivery by Using Polymeric Nanoparticles, Pharmacological Reviews, 2012, pFWA 505-519.*
Perica et al, Linking form to function: Biophysical aspects of artificial antigen presenting cell design, Biochimica et Biophysica Acta 1853 (2015) 781-790.*
Sunshine Joel C et al: "Particle shape dependence of CD8+ T cell activation by artificial antigen presenting cells", Biomaterials, vol. 35, No. 1, Oct. 5, 2013, pp. 269-277.
Loek J. Eggermont et al: "Towards efficient cancer immunotherapy: advances in developing artificial antigen-presenting cells", Trends in Biotechnology, vol. 32, No. 9, Sep. 1, 2014, pp. 456-465.
The partial supplementary European search report dated Jun. 22, 2015 from corresponding European patent application No. 12856501.
The extended European search report dated Oct. 13, 2015 from corresponding European patent application No. 12856501.
Balmert, S.C. & Little, S.R. Biomimetic delivery with micro- and nanoparticles. Adv Mater 24, 3757-3778 (2012).
Batycky, R.P., Hanes, J., Langer, R. & Edwards, D.A. A theoretical model of erosion and macromolecular drug release from biodegrading microspheres. J Pharm Sci 86, 1464-1477 (1997).

(Continued)

*Primary Examiner* — Maria Marvich
(74) *Attorney, Agent, or Firm* — Casimir Jones, S.C.; Jeffrey W. Childers

(57) ABSTRACT

Compositions and methods comprising asymmetrical artificial antigen presenting cells (aAPCs) are disclosed. The non-spherical aAPCs more closely mimic endogenous cell-cell interactions and can be used for antigen-specific immunotherapy.

18 Claims, 21 Drawing Sheets

(56) References Cited

OTHER PUBLICATIONS

Bullock, T.N.J., D.W. Mullins, and V.H. Engelhard. 2003. Antigen density presented by dendritic cells in vivo differentially affects the number and avidity of primary, memory, and recall CD8+ T cells. Journal of Immunology. 170: 1822-9. (2003).
Champion, J.A. & Mitragotri, S. Role of target geometry in phagocytosis. Proc Natl Acad Sci U S A 103, 4930-4934 (2006).
Champion, J.A., Katare, Y.K. & Mitragotri, S. Particle shape: a new design parameter for micro- and nanoscale drug delivery carriers. J Control Release 121, 3-9 (2007).
Chang, T. M. S. (2004). Artificial Cell Bioencapsulation in Macro, Micro, Nano, and Molecular Dimensions: Keynote Lecture. Artificial Cells, Blood Substitutes and Biotechnology 32(1): 1-23.
Chiu YL, Schneck JP, and Oelke M. HLA-Ig based artificial antigen presenting cells for efficient ex vivo expansion of human CTL. J Vis Exp. Apr. 11, 2011;(50). Pii:2801:do1: 10.3791/2801.
Curtsinger, J., Deeths, M.J., Pease, P. & Mescher, M.F. Artificial cell surface constructs for studying receptor-ligand contributions to lymphocyte activation. J Immunol Methods 209, 47-57 (1997).
Devarajan PV, Jindal AB, Patil RR, Mulla F, Gaikwad RV, Samad A.Particle shape: a new design parameter for passive targeting in splenotropic drug delivery. J Pharm Sci 99, 2576-2581 (2010).
Durai, M., C. Krueger, Z. Ye, L. Cheng, A. Mackensen, et al. 2009. In vivo functional efficacy of tumor-specific T cells expanded using HLA-Ig based artificial antigen presenting cells (aAPC). Cancer immunology, immunotherapy: CII. 58: 209-220.
Grakoui, A., et al., The immunological synapse: a molecular machine controlling T cell activation. Science 285, 221-227 (1999).
Han H, Peng JR, Chen PC, Gong L, Qiao SS, Wang WZ, Cui ZQ, Yu X, Wei YH, Leng XS. A novel system of artificial antigen-presenting cells efficiently stimulates Flu peptide-specific cytotoxic T cells in vitro. Biochem Biophys Res Commun 411, 530-535 (2011).
Harris, B.J. & Dalhaimer, P. Particle shape effects in vitro and in vivo. Front Biosci (Schol Ed) 4, 1344-1353 (2012).
Ito F, Carr A, Svensson H, Yu J, Chang AE, Li Q. Antitumor reactivity of anti-CD3/anti-CD28 bead-activated lymphoid cells: implications for cell therapy in a murine model. J Immunother 26, 222-233 (2003).
Kroger, C.J. and Alexander-Miller, M.A., Cutting edge: CD8+ T cell clones possess the potential to differentiate into both high- and low-avidity effector cells. J Immunol 179, 748-751 (2007).
Lee JB, Oelke M, Ramachandra L, Canaday, and Schneck JP. Decline of influenza-specific CD8+ T cell repertoire in healthy geriatric donors. Immun Ageing Aug. 16, 2011, 8:6.
Lee, K.H., et al. T cell receptor signaling precedes immunological synapse formation. Science 295, 1539-1542. (2002).
Levine, B.L., et al., Effects of CD28 costimulation on long-term proliferation of CD4+ T cells in the absence of exogenous feeder cells. J Immunol 159, 5921-5930. (1997).
Li Y, Tao SC, Zhu H, and Schneck JP. High-throughput lectin microarray-based analysis of live cell surface glycosylation. Curr Protoc Protein Sci. Feb. 2011;Chapter 12:Unit 12/9.
Lum, L.G., LeFever, A.V., Treisman, J.S., Garlie, N.K. & Hanson, J.P., Jr. Immune modulation in cancer patients after adoptive transfer of anti-CD3/anti-CD28- costimulated T cells-phase I clinical trial. J Immunother 24, 408-419 (2001).
Maus, M.V., et al., Ex vivo expansion of polyclonal and antigen-specific cytotoxic T lymphocytes by artificial APCs expressing ligands for the T cell receptor, CD28 and 4-1BB. Nat Biotechnol 20, 143-148. (2002).
Meng, F., G. H. M. Engbers, et al. (2005). Biodegradable polymersomes as a basis for artificial cells: encapsulation, release and targeting. Journal of Controlled Release 101(1-3): 187-198.
Meng, F., Z. Zhong, et al. (2009). Stimuli-Responsive Polymersomes for Programmed Drug Delivery. Biomacromolecules 10(2): 197-209.
Mescher, M.F. Surface contact requirements for activation of cytotoxic T lymphocytes. J Immunol 149, 2402-2405 (1992).
Monks, C.R., Freiberg, B.A., Kupfer, H., Sciaky, N. & Kupfer, A. Three-dimensional segregation of supramolecular activation clusters in T cells. Nature 395, 82-86 (1998).
Ndhlovu, Z, Angenendt M, Heckel D, Schneck, JP, Griffin DE and Oelke M. Development of artificial antigen-presenting cell (aAPC)-based assay for the detection of low frequency virus- specific CD8+4 Tcells in whole blood with application to measles virus. Clin Vaccine Immunol. 2009.
Ndhlovu, Z.M., Oelke, M., Schneck, J.P. & Griffin, D.E. Dynamic regulation of functionally distinct virus-specific T cells. Proc Natl Acad Sci U S A 107, 3669-3674 (2010).
Rothstein, S.N., Federspiel, W.J. & Little, S.R. A unified mathematical model for the prediction of controlled release from surface and bulk eroding polymer matrices. Biomaterials 30, 1657-1664 (2009).
Schneck, J.P., J.E. Slansky, S.M. O'Herrin, and T.F. Greten. 2001. Monitoring antigen-specific T cells using MHC-Ig dimers. Current protocols in immunology / edited by John E. Coligan . . . [et al.]. Chapter 17: Unit 17.2.
Schuetz C, Fleck M, Mackensen A, Zoso A, Halbritter D, Schneck JP, and Oelke M. Killer artificial antigen-presenting cells: A novel strategy to delete specific T cells. Blood 2008. Apr. 1;111(7)3546-52. Epub Dec. 20, 2007.
Schuetz C, Oelke M, Schneck JP, Mackensen A, and Fleck, M. Killer artificial antigen-presenting cells: The synthetic embodiment of a "guided missile." Immunotherapy Jul. 2010;2(4):539-50.
Seder, R.A., Darrah, P.A. & Roederer, M. T cell quality in memory and protection: implications for vaccine design. Nat Rev Immunol 8, 247-258 (2008).
Shaikh SR, Mitchell D, Carroll E, Li M, Schneck J.P., and Edidin M. Differential effects of a saturated and a monounsaturated fatty acid on MHC> class I antigen presentation. Scand. J. Immunol. Jul. 2008;68(1):30-42.
Sharma G, Valenta DT, Altman Y , Harvey S, Xie H, Mitragotri S, Smith JW. Polymer particle shape independently influences binding and internalization by macrophages. J Control Release 147, 408-412 (2010).
Steenblock, E.R. & Fahmy, T.M. A comprehensive platform for ex vivo T cell expansion based on biodegradable polymeric artificial antigen-presenting cells. Mol Ther 16, 765-772. PMID: 18334990 (2008).
Steenblock, E.R., Fadel, T., Labowsky, M., Pober, J.S. & Fahmy, T.M. An artificial antigen-presenting cell with paracrine delivery of IL-2 impacts the magnitude and direction of the T cell response. J Biol Chem 286, 34883-34892 (2011).
Taylor, P.A., Lees, C.J. & Blazar, B.R. The infusion of ex vivo activated and expanded CD4(+)CD25(+) immune regulatory cells inhibits graft-versus-host disease lethality. Blood 99, 3493-3499 (2002).
Ugel S, Zoso A, De Santo C, Li Y, Mango I, Zanovello P, Scarselli E, Cipriani B, Oelke M, Schneck JP, Bronte V. In vivo administration of artificial antigen-presenting cells activates low-avidity T cells for treatment of cancer. Cancer Res 69, 9376-9384 (2009).
Von Burkersroda, F., Schedl, L. & Gopferich, A. Why degradable polymers undergo surface erosion or bulk erosion. Biomaterials 23, 4221-4231 (2002).
Wang, J., Byrne, J.D., Napier, M.E. & DeSimone, J.M. More effective nanomedicines through particle design. Small 7, 1919-1931 (2011).
Webb T, Giuntoli R, Rogers O, Schneck J.P. Oelke M. Ascites Specific Inhibition of CD1d-Mediated Activation of NKT cells. Clinical Cancer Research. 2008.
Webb, T, Bieler, J, Schneck, JP, Oelke, M. Ex vivo induction and expansion of Natural Killer T cells be CD1d1-Ig coated artificial antigen presenting cells. J Immunol Methods 2009. May 14.
Weisstein, E.W. "Prolate Spheroid." From MathWorld—A Wolfram Web Resource. http://mathworld. wolfram. com/ProlateSpheroid. html (2009).
Xiao Z, Mohamood AS, Uddin S, Gutfreund R, Nakata C, Marshall A, Kimura H, Caturegli P, Womer KL, Huang Y, Jie C, Chakravarti S, Schneck JP, Yagita and Hamad AR. Inhibition of Fas ligand in

(56) References Cited

OTHER PUBLICATIONS

NOD mice unmasks a protective role for IL-10 against insulitis development. Am J Pathol. Aug. 2011;179(2):725-32.
Yoo, J.W. & Mitragotri, S. Polymer particles that switch shape in response to a stimulus. Proc Natl Acad Sci U.S.A 107, 11205-11210 (2010).
International Search Report and Written Opinion dated Mar. 28, 2013 from International Patent Application No. PCT/US2012/068759.
Oelke M, Maus MV, Didiano D, Jun. CH, Mackensen A, Schneck JP. Ex vivo induction and expansion of antigen-specific cytotoxic T cells by HLA-Ig-coated artificial antigen-presenting cells. Nat Med 9, 619-625. PMID: 12074385 (2003).
Steenblock, E.R., Wrzesinski, S.H., Flavell, R.A. & Fahmy, T.M. Antigen presentation on artificial acellular substrates: modular systems for flexible, adaptable immunotherapy. Expert Opin Biol Ther 9, 451-464. PMID: 19344282 (2009).

* cited by examiner

ARTIFICIAL ANTIGEN PRESENTING CELLS HAVING A DEFINED AND DYNAMIC SHAPE

CROSS-REFERENCE TO RELATED APPLICATIONS

This application is a 35 U.S.C. § 371 U.S. national phase entry of International Application No. PCT/US2012/068759 having an international filing date of Dec. 10, 2012, which claims the benefit of U.S. Provisional Application No. 61/568,751, filed Dec. 9, 2011. The content of each of the aforementioned applications is herein incorporated by reference in its entirety.

BACKGROUND

Geometry and spatial organization are critical components in many biological systems. The importance of geometry and spatial organization can be seen within the immune system in a variety of ways including during the interaction of a T cell with an antigen presenting cell (APC), which is a critical determinant of T cell fate and effector function. With activation, APC, such as dendritic cells (DC), have major changes in their cell morphology, which results in a significant increase in their overall cell surface area. Such changes in cell morphology facilitate interaction with naïve T cells and ultimately affect T cell fate and outcome. T cell activation is further modulated by the formation of a large surface area of close membrane apposition between the DC and T cell membrane termed the "immune synapse." Grakoui, A., et al., The immunological synapse: a molecular machine controlling T cell activation. Science 285, 221-227 (1999). Monks, C. R., et al., Three-dimensional segregation of supramolecular activation clusters in T cells. Nature 395, 82-86 (1998). Lee, K. H., et al., T cell receptor signaling precedes immunological synapse formation. Science 295, 1539-1542 (2002). Thus, taking into account the geometry and spatial organization is important in studying biological responses.

Reductionist systems also have facilitated the study of effective immune responses. One such system has been the development of acellular artificial antigen presenting cells (aAPCs). These systems have been made by coupling proteins required for T cell activation to particles. Minimally, T cell activation requires two sets of receptor-receptor interactions between cells. The first interaction, Signal 1, is the binding of major histocompatibility complexes (MHC) or a surrogate, such as anti-CD3, to the T cell receptor (TCR). The second interaction, Signal 2, is the binding of costimulatory receptors on the APC, such as B7.1, to ligands on the T cell, such as CD28. Accordingly, aAPC have been generated by coupling proteins that deliver Signal 1 and Signal 2 to the surface of microbeads (FIG. 2a) made from a range of materials, including magnetic microparticles, Oelke, M., et al., Ex vivo induction and expansion of antigen-specific cytotoxic T cells by HLA-Ig-coated artificial antigen-presenting cells. Nat Med 9, 619-625. PMID: 12074385 (2003). Ugel, S., et al., In vivo administration of artificial antigen-presenting cells activates low-avidity T cells for treatment of cancer. Cancer Res 69, 9376-9384 (2009), polystyrene particles, Mescher, M. F. Surface contact requirements for activation of cytotoxic T lymphocytes. J Immunol 149, 2402-2405 (1992), and PLGA microparticles. Han, H., et al., A novel system of artificial antigen-presenting cells efficiently stimulates Flu peptide-specific cytotoxic T cells in vitro. Biochem Biophys Res Commun 411, 530-535 (2011). Steenblock, E. R., et al., An artificial antigen-presenting cell with paracrine delivery of IL-2 impacts the magnitude and direction of the T cell response. J Biol Chem 286, 34883-34892 (2011). Steenblock, E. R. and Fahmy, T. M. A comprehensive platform for ex vivo T cell expansion based on biodegradable polymeric artificial antigen-presenting cells. Mol Ther 16, 765-772. PMID: 18334990 (2008).

Such systems have been broadly applied to tumor immunotherapy, vaccination, and immunosuppression, and are amenable to in vivo or ex vivo T cell stimulation and offer possible novel translational approaches to immunotherapy. Ugel, S., et al., In vivo administration of artificial antigen-presenting cells activates low-avidity T cells for treatment of cancer. Cancer Res 69, 9376-9384 (2009). Ndhlovu, Z. M., et al., Dynamic regulation of functionally distinct virus-specific T cells. Proc Natl Acad Sci USA 107, 3669-3674 (2010). Ito, F., et al., Antitumor reactivity of anti-CD3/anti-CD28 bead-activated lymphoid cells: implications for cell therapy in a murine model. J Immunother 26, 222-233 (2003). Lum, L. G., et al., Immune modulation in cancer patients after adoptive transfer of anti-CD3/anti-CD28-co-stimulated T cells-phase I clinical trial. J Immunother 24, 408-419 (2001). Taylor, P. A., et al., The infusion of ex vivo activated and expanded CD4(+)CD25(+) immune regulatory cells inhibits graft-versus-host disease lethality. Blood 99, 3493-3499 (2002). Balmert, S. C. and Little, S. R., Biomimetic delivery with micro- and nanoparticles. Adv Mater 24, 3757-3778 (2012).

While useful, the Signal 1 and Signal 2 paradigms alone do not capture aspects of spatial organization or the geometry of interactions. Previous work developing artificial systems for stimulation of effective in vitro and in vivo T cell responses has not attempted to re-capitulate these aspects of APC behavior. As a result, all particle systems tested thus far have used spherical particles for their aAPC platforms, which unlike DC, minimize surface area for a given volume (FIG. 2b).

Particle shape has only recently become a design parameter of interest in the field of material design for drug delivery. Shape can play a role in tuning the rate and mechanism of cellular uptake, Wang, J., et al., More effective nanomedicines through particle design. Small 7, 1919-1931 (2011), can dramatically reduce internalization by phagocytic cells, such as macrophages, Champion, J. A. and Mitragotri, S., Role of target geometry in phagocytosis. Proc Natl Acad Sci USA 103, 4930-4934 (2006). Sharma, G., et al., Polymer particle shape independently influences binding and internalization by macrophages. J Control Release 147, 408-412 (2010), can change the biodistribution of the drug delivery vehicle, Champion, J. A., et al., Particle shape: a new design parameter for micro- and nanoscale drug delivery carriers. J Control Release 121, 3-9 (2007). Devarajan, P. V., et al., Particle shape: a new design parameter for passive targeting in splenotropic drug delivery. J Pharm Sci 99, 2576-2581 (2010), and can affect the ability of a particle to bind a cell, in part, by increasing the surface area for interaction. Champion, J. A., et al., Particle shape: a new design parameter for micro- and nanoscale drug delivery carriers. J Control Release 121, 3-9 (2007). Harris, B. J. and Dalhaimer, P., Particle shape effects in vitro and in vivo. Front Biosci (Schol Ed) 4, 1344-1353 (2012). Yoo, J. W. and Mitragotri, S., Polymer particles that switch shape in response to a stimulus. Proc Natl Acad Sci USA 107, 11205-11210 (2010)

SUMMARY

In some aspects, the presently disclosed subject matter provides an artificial antigen presenting cell (aAPC) comprising: (a) a three-dimensional microparticle or nanoparticle having an asymmetrical shape that mimics a shape of a cell or a microorganism; and (b) one or more molecules capable of interacting with one or more T cell receptors (TCRs) of a T cell. In certain aspects, the cell or a microorganism is selected from the group consisting of a bacterium, an archaeon, a protozoan, a fungus, an algae, and a virus. In some aspects, the cell or microorganism has a shape selected from the group consisting of a spiral, a cube, a rod, a comma, a star, a square, a column, a polyhedran, a helix, an icosahedran, a cylinder, a tetrahedron, and a pyramid.

In other aspects, the presently disclosed subject matter provides an artificial antigen presenting cell (aAPC) comprising: (a) a three-dimensional microparticle or nanoparticle having an asymmetrical shape, wherein the asymmetrical shape has at least one surface having a radius of curvature along at least one axis which is in one of the following ranges: (a) about 1 nm to about 10 nm; (b) about 11 nm to about 100 nm; (c) about 101 nm to about 400 nm; (d) about 401 nm to about 1 µm; (e) about 10 µm to about 20 µm; (f) about 20 µm to about 100 µm; and (g) about 101 µm to about-1 mm; and (b) one or more molecules capable of interacting with one or more T cell receptors (TCRs) of a T cell.

In yet other aspects, the presently disclosed subject matter provides an artificial antigen presenting cell (aAPC) comprising (a) a three-dimensional microparticle or nanoparticle having an asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c); and (b) one or more molecules capable of interacting with one or more T cell receptors (TCRs) of a T cell. In particular aspects, the asymmetrical shape comprises an ellipsoid, which can be described by one of the following equations: a>b=c (prolate ellipsoid); a>b>c (tri-axial ellipsoid); and a=b>c (oblate ellipsoid).

In another aspect, the presently disclosed subject matter provides a method for modulating a T cell, the method comprising (a) providing an artificial antigen presenting cell (aAPC) comprising: (i) a three-dimensional microparticle or nanoparticle having an asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c); and (ii) one or more molecules capable of interacting with one or more T cell receptors (TCRs) of a T cell and one or more molecules capable of interacting with a receptor other than a TCR on the T cell to costimulate the T cell; (b) contacting the T cell with the aAPC; and (c) allowing the T cell to be modulated.

In still another aspect, the presently disclosed subject matter provides a method for making an artificial antigen presenting cell (aAPC) comprising a three-dimensional microparticle or nanoparticle having an asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c); and one or more molecules capable of interacting with one or more T cell receptors (TCRs) of a T cell, the method comprising (a) providing or preparing a plurality of microparticles or nanoparticles; (b) preparing a film comprising the plurality of microparticles or nanoparticles; (c) stretching the film comprising the plurality of microparticles or nanoparticles to form a plurality of three-dimensional microparticles or nanoparticles having an asymmetrical shape; (d) harvesting the plurality of three-dimensional microparticles or nanoparticles having an asymmetrical shape; and (e) coupling to the plurality of three-dimensional microparticles or nanoparticles having an asymmetrical shape one or more molecules capable of interacting with one or more T cell receptors (TCRs) of a T cell.

In yet further aspects, the presently disclosed subject matter provides a device for stretching a film.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 5:
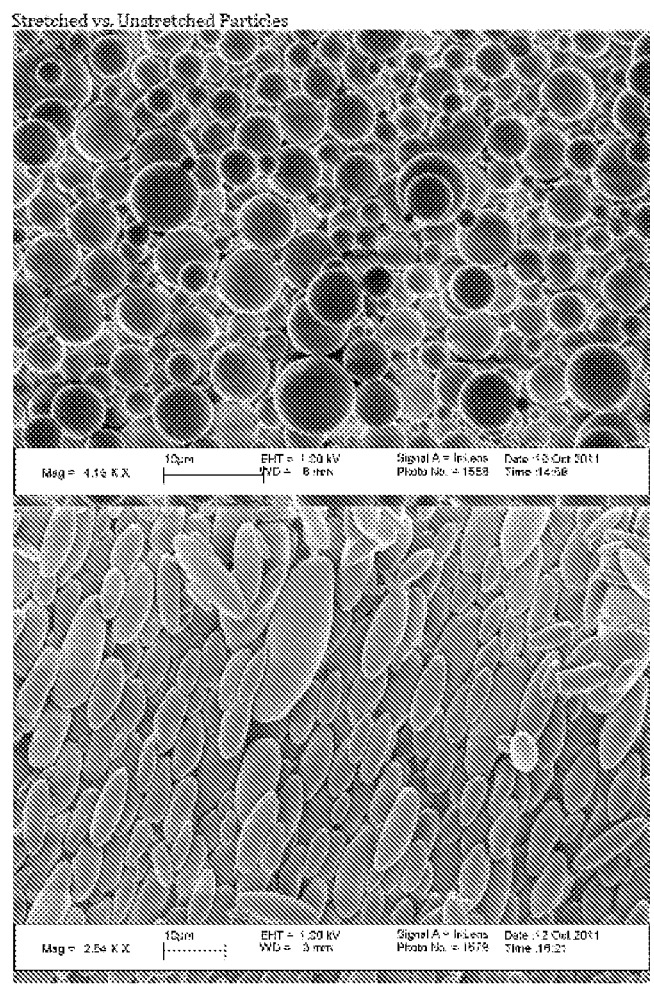
Figure 6:
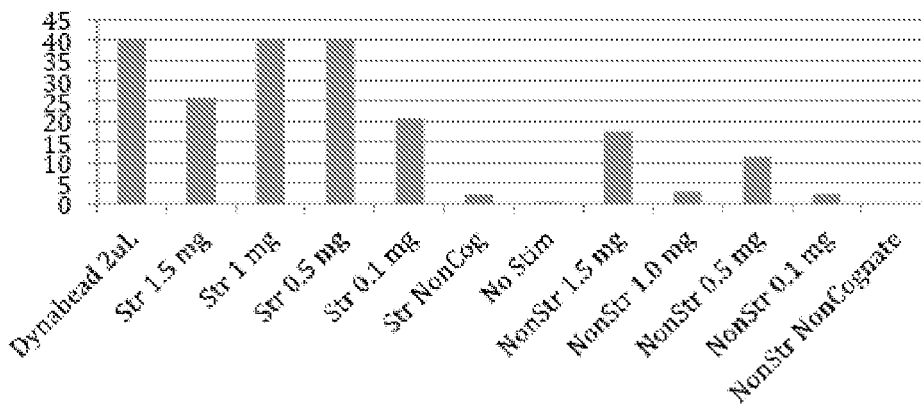
Figure 6:
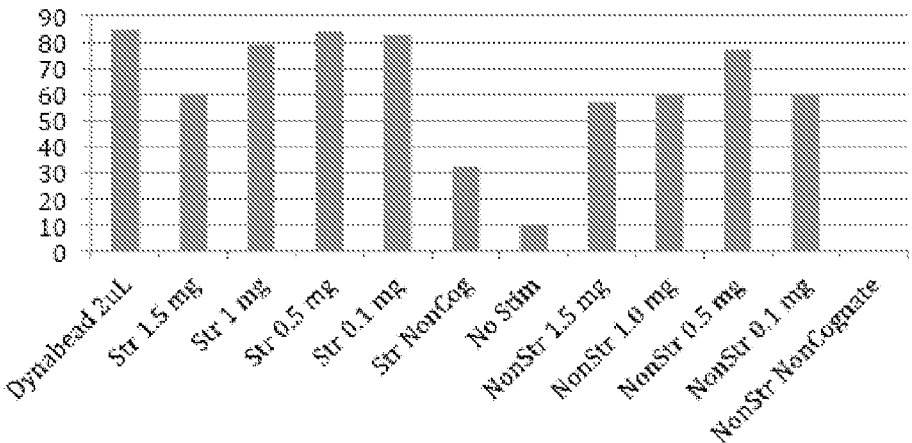
Figure 7:
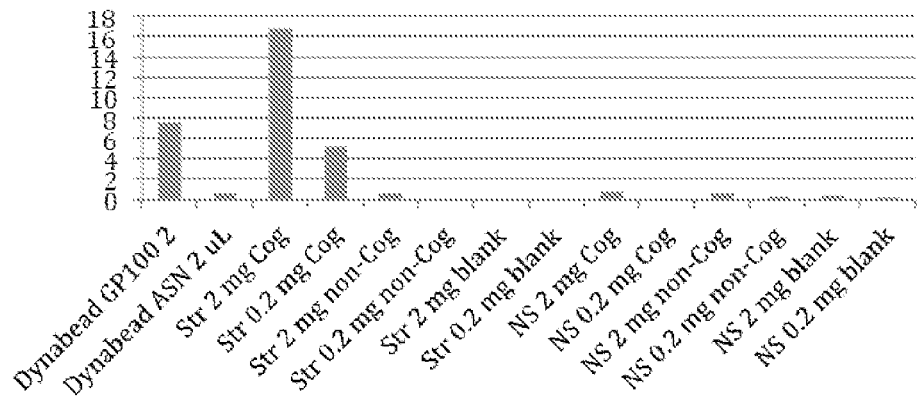
Figure 7:
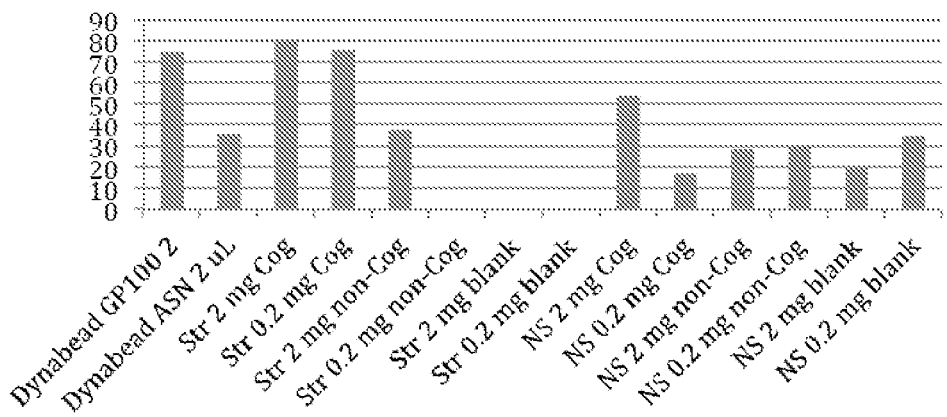
Figure 9:
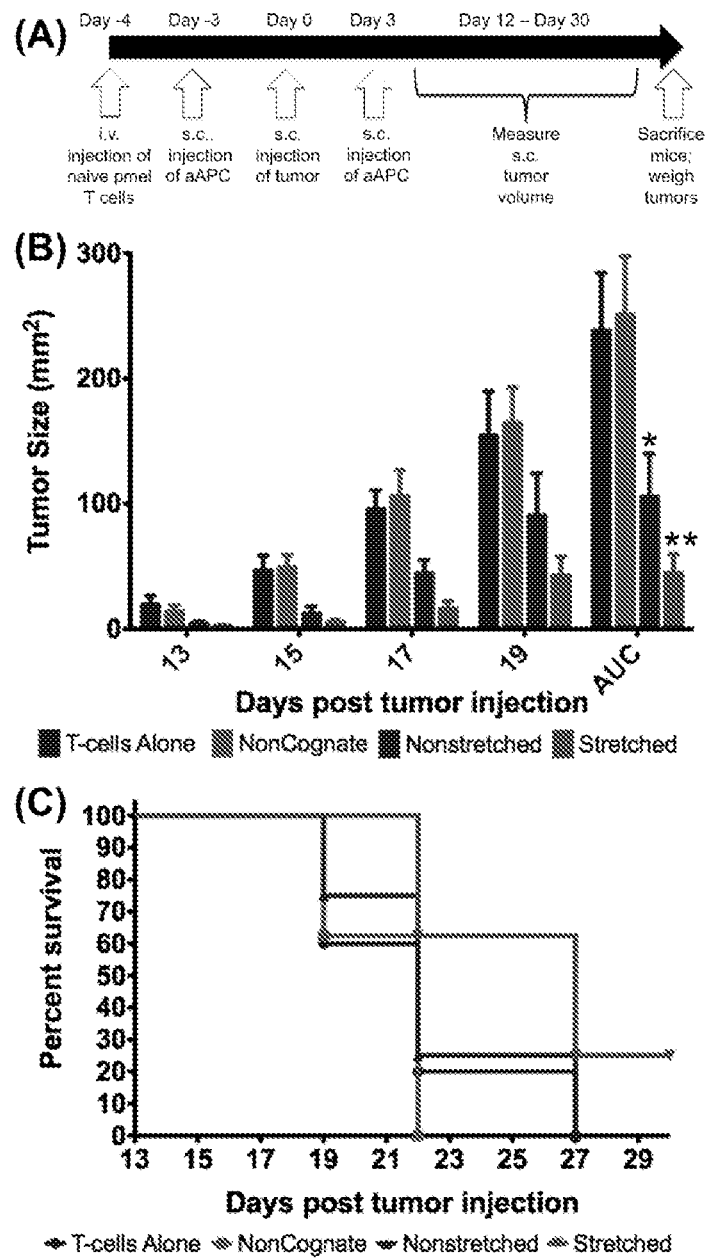
Figure 11:
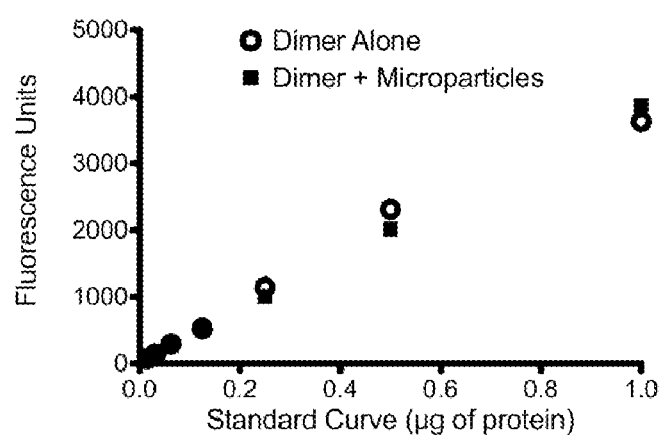
Figure 14:
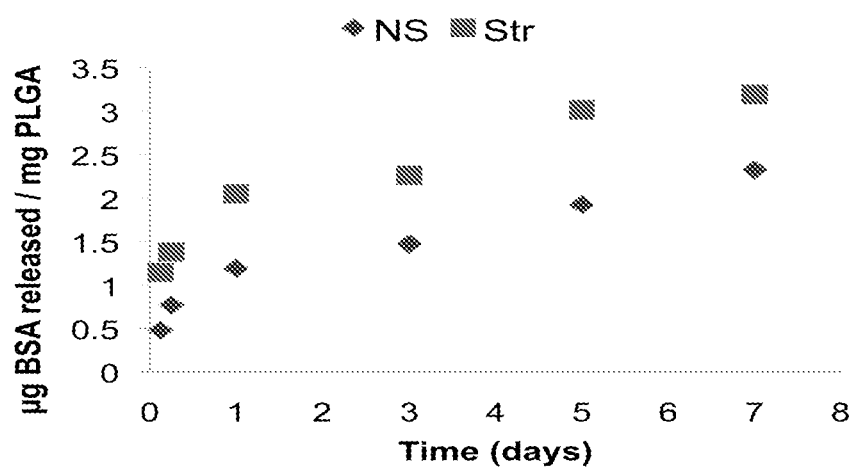
Figure 15:
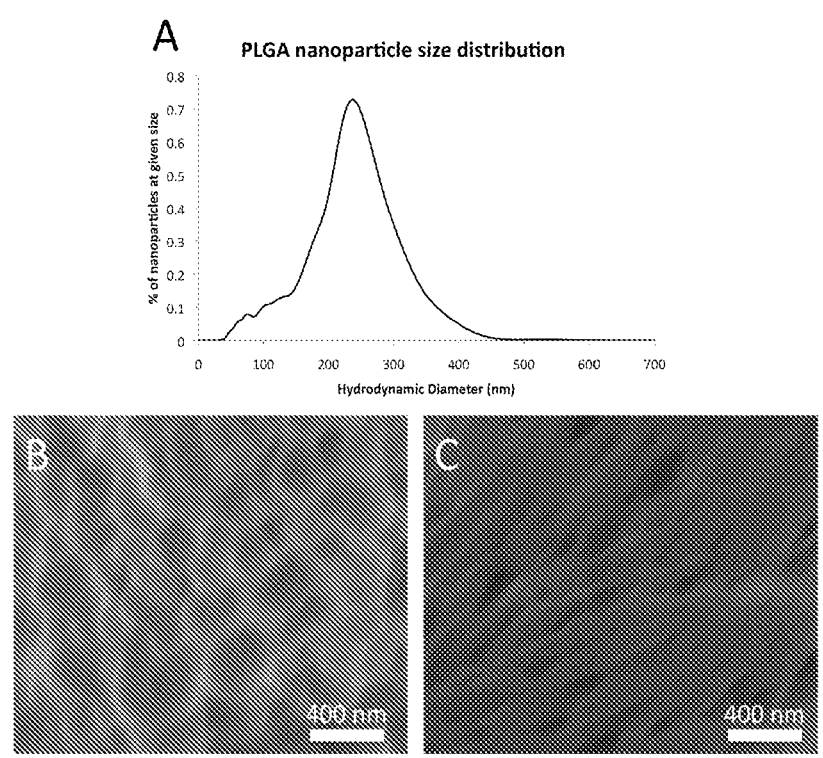
Figure 16:
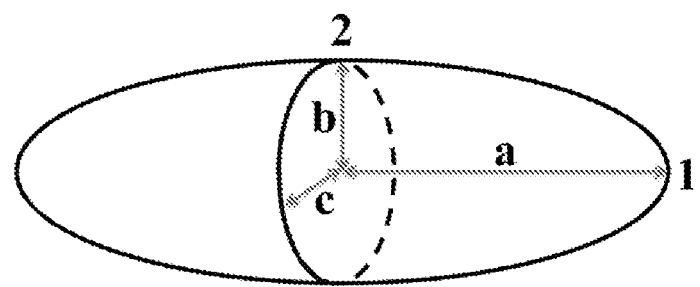
Figure 17:
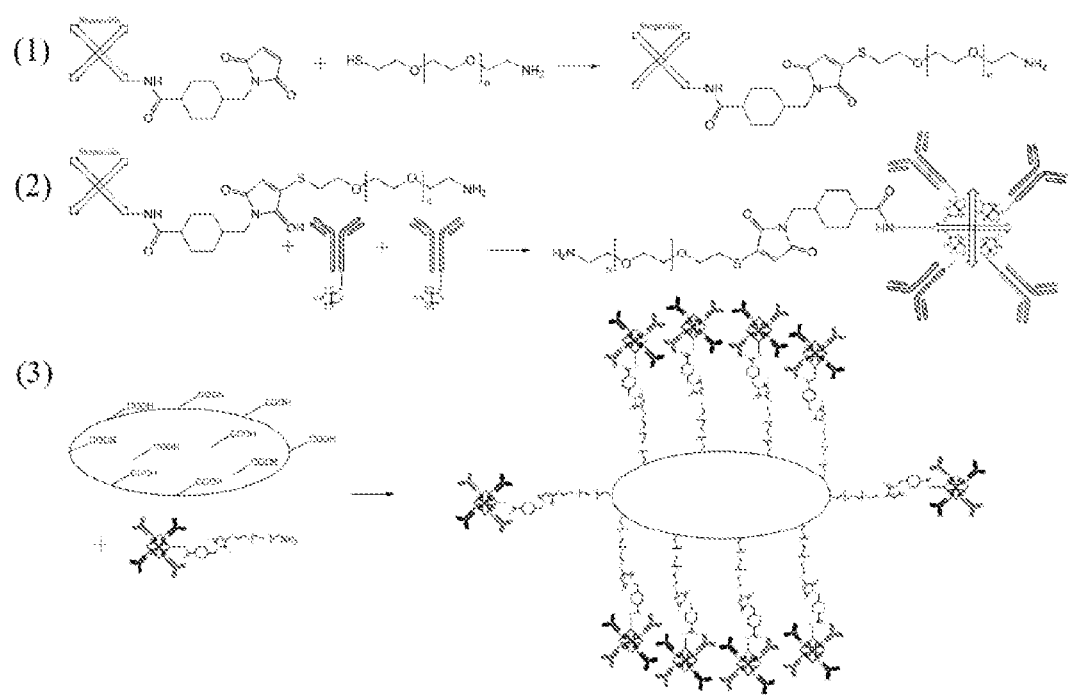

Having thus described the presently disclosed subject matter in general terms, reference will now be made to the accompanying Figures, which are not necessarily drawn to scale, and wherein:

FIG. 1 shows representative embodiments of the presently disclosed artificial cell parameters that can be changed and the methodology for achieving the changes;

FIGS. 2A-2I are (A) a schematic of an aAPC; (B-D) schematics of the interaction between a T cell, modeled as a sphere, interacting with (B) a sphere; (C) an ellipsoid (AR 2.83; stretch ratio 2); and (D) an antigen presenting cell (APC); (E) characterization by SEM (2000× magnification) of spherical and ellipsoidal PLGA microparticles (scale bar corresponds to 10 µm); (F) size distribution of microparticles; (G) comparison of degree of stretch imposed on the film (STR) with the aspect ratio (AR) of the generated ellipsoidal microparticles (predicted AR=STR$^{3/2}$); (H) Coupling efficiency for protein during synthesis of aAPC from spherical and ellipsoidal microparticles (n=2); and (I) protein release from the surface of microparticles at 37° C. in PBS (pH 7.4) over the course of one week;

FIGS. 3A-3D show specific T cell proliferation in response to specified aAPC dose, protein density, and shape of aAPC: (Top) CFSE dilution data for stretched (Str, solid line) and non-stretched particles (NS, dashed line) at the highest protein dose (4 µg dimer/mg PLGA during conjugation) at 3 doses of particles (B1-D1) compared to non-cognate (A); (B2-D2) T cell proliferation (fold expansion/100,000 cells) 7 days after particle addition to T cells with indicated doses, shapes (stretched/non-spherical in black, non-stretched/spherical in white), and protein densities;

FIGS. 4A-4C show T cell response to particles which have been stretched different amounts. Specific T cell proliferation in response to 0.01 mg particles/100,000 cell dose for aAPCs with different applied stretch: (A) CFSE dilution after exposure to differentially stretched aAPCs; (B) fraction of cells which underwent 0-1, 2-3, 4-5, 6-7 rounds of proliferation for differentially stretched aAPCs; and (C) T cell proliferation (fold expansion/100,000 cells) 7 days after aAPC addition to T cells;

FIG. 5 shows scanning electron micrographs of non-stretched (top) or stretched (bottom) PLGA microparticles;

FIGS. 6A-6B show (a) T cell proliferation (fold expansion/100,000 cells) 5 days after aAPC addition to T cells; and (b) T cell viability 5 days after aAPC addition to T cells; Str=stretched, Nonstr=nonstretched;

FIGS. 7A-7B show (a) T cell proliferation (fold expansion/100,000 cells) 7 days after aAPC addition to T cells; and (b) T cell viability 7 days after aAPC addition to T cells; Str=stretched, NS=nonstretched;

FIGS. 8A-8G show confocal imaging of aAPC (green) conjugate formation to T cells (red): (A) conjugates appear as areas of close membrane apposition between cells and the particles, with T cell morphology rearrangement into a distinctive cap; (B) non-stretched; and (C) stretched aAPC form cell-bead conjugates, which are more frequently observed with stretched aAPC; (D-E) conjugate formation is not observed with particles bearing non-cognate MHC-peptide; (F) 4.634±0.9% of T cells incubated with stretched aAPC compared to 1.78±043% with non-stretched were observed to have formed conjugates (p=0.01); and (E) time-lapse image of a single T cell interacting with one stretched, non-spherical cognate aAPC; images acquired two seconds apart;

FIGS. 9A-9C show an in vivo tumor-prevention model: (A) experimental protocol and timeline; (B) tumor size measurements for mice injected with cancer and T cells alone or also injected with non-cognate stretched (NonCognate), cognate non-stretched (Nonstretched), and cognate stretched particles (Stretched). AUC=area under the curve. * p=0.02 vs. non-cognate; ** p=0.0009 vs. non-cognate. For comparison of stretched cognate and non-stretched cognate, p=0.13; and (C) survival curve-mice were sacrificed and declared "dead" when tumor size reached 200 mm$^2$. Subcutaneous injection of stretched particles resulted in increased survival vs. non-stretched cognate particles (p=0.05), stretched non-cognate particles (p=0.004), and T cells alone (p=0.05);

FIGS. 10A-10D demonstrate that aAPCs do not change their shape in physiological conditions over one week: Scanning electron micrograph (SEM) of freshly prepared aAPCs (a) and aAPCs incubated in PBS at 37° C. for (b) 1 day, (c) 3 days, (d) 7 days. Calculated aspect ratios: (a) 3.71, (b) (c) (d);

FIG. 11 shows standard curves for fluorescently labeled MHC dimer or for dimer+2 mg microparticles per well;

FIGS. 12A-12C show fold expansion of PMEL T cells post incubation with (A) 0.01 mg/100,000 cells, (B) 0.1 mg/100,000 cells, and (C) 1 mg/100,000 cells of differentially stretched aAPC as indicated. Negative controls with non-cognate peptide-in-MHC showed no expansion;

FIGS. 13A-13B show intracellular cytokine staining after stimulation of aAPC-activated T cells. (A) CD107a and (B) IFN-gamma. CD8+ isolated splenocytes were activated with 0.1 mg Non-Stretched, spherical aAPC (filled circle), 0.1 mg of Stretched, non-spherical aAPC (filled square), or 0.01 mg of Stretched, non-spherical aAPC (unfilled square). Seven days later, T cells were restimulated with splenocytes from C57BLACK6 mice pulsed with the indicated dose of cognate GP100 peptide. Unpulsed splenocytes (No Peptide) or no splenocytes (No Stim) were used as controls. Cytokine production is reported as percentage of T cells making indicated cytokine;

FIG. 14 shows BSA release from non-stretched (NS) and 2-fold stretched (Str; aspect ratio=2.8) microparticles incubated at 37° C. in PBS for the indicated amount of days. Data presented represent a cumulative release from the microparticles as measured by the BCA assay;

FIGS. 15A-15C show: (a) PLGA nanoparticle size by distribution from NanoSight; (b,c) Scanning electron micrographs of non-stretched (b) or stretched (c) PLGA nanoparticles;

FIG. 16 is a prolate ellipsoid (a>b=c) with axes labeled and key points numbered;

FIG. 17 shows an embodiment of the formation of "hyperdense" ligand coated particles; and FIGS. 18A-18D show embodiments of a representative device for use in creating the presently disclosed aAPCs.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. ARTIFICIAL ANTIGEN PRESENTING CELLS

Control of biological cells is crucial for the study and treatment of many diseases. The presently disclosed subject matter achieves cellular control by developing an innovative class of synthetic micro- and nano-sized particles that mimic the function of target cells. These artificial/synthetic cells are engineered in new ways so that the following parameters are able to be tuned independently: size of the artificial cells, shape of the artificial cells, composition and location of proteins immobilized to the cell surface, composition of soluble factors released from the artificial cells, the time course of this drug release, and the time scale of the biodegradation of the artificial cells themselves (FIG. 1). These synthetic micro- and nano-particles are composed of biodegradable polymers and could be used in many areas of cell engineering to significantly advance biomedical science.

Specific applications of the artificial cells include their use as artificial antigen presenting cells. The artificial antigen presenting cells could potentially enable new treatments for infectious diseases and cancer. The creation of a new biomaterial class of synthetic micro- and nano-particles that mimic the function(s) of target cells could potentially have both scientific and translational impact.

Previous work developing particle-based acellular, artificial antigen presenting cells (aAPCs) has focused exclusively on spherical platforms. The geometry of the interaction between an activated antigen presenting cell and a T cell, however, is quite different from that of two interacting spheres. To explore the role of shape in this process, the presently disclosed subject matter adopts the approach of altering the shape of microparticles or nanoparticles, e.g., in some embodiments, PLGA microparticles, to generate ellipsoidal microparticles having varying long axis lengths and aspect ratios (ARs). The presently disclosed "stretched" biomimetic non-spherical aAPCs with high AR showed significantly enhanced activity above that seen with spherical aAPCs with particle volume and antigen content held constant.

Without wishing to be bound to any one particular theory, confocal imaging indicates that this effect may be due to improved interaction along the long axis of the stretched aAPCs and that T cells will preferentially migrate to and are activated by interaction with the long axis of the particle. Enhanced activity of non-spherical, high-aspect ratio aAPCs also was observed in vivo with high-aspect ratio aAPCs which, in a representative example, improved melanoma survival compared to non-cognate aAPCs (p=0.004), as well as cognate spherical aAPCs (p=0.05). The presently disclosed subject matter indicates that particle geometry is a critical design criterion in the generation of aAPCs and provides insights into the essential role of geometry involved in the interaction between T cells and biological APCs.

Accordingly, in some embodiments, the presently disclosed subject matter provides an artificial antigen presenting cell (aAPC) comprising: (a) a three-dimensional microparticle or nanoparticle having an asymmetrical shape that mimics a shape of a cell or a microorganism; and (b) one or more molecules capable of interacting with one or more T cell receptors (TCRs) of a T cell. In certain embodiments, the cell or a microorganism is selected from the group consisting of a cell, a bacterium, and a virus.

As used herein, the term "microorganisms" refers to unicellular organisms, such as the prokaryotes, including bacteria and archaea, single-celled protozoa, single-celled fungi, single-celled algae, and viruses.

Examples of shapes of cells or microorganisms include, but are not limited to, spiral, cube-like, rod, comma-shaped, star shaped, square, columnar, polyhedral, helical, icosahedral, cylindrical, tetrahedron, and pyramid.

In other embodiments, the presently disclosed subject matter provides an artificial antigen presenting cell (aAPC) comprising: (a) a three-dimensional microparticle or nanoparticle having an asymmetrical shape, wherein the asymmetrical shape has at least one surface having a radius of curvature along at least one axis which is in one of the following ranges: (a) 1 nm-10 nm; (b) 11 nm-100 nm; (b) 101 nm-400 nm; (c) 401 nm-1 μm; (d) 10 μm-20 μm; (e) 20 μm-100 μm (f) 101 μm-1 mm; and (b) one or more molecules capable of interacting with one or more T cell receptors (TCRs) of a T cell.

In yet other embodiments, the presently disclosed subject matter provides an artificial antigen presenting cell (aAPC) comprising (a) a three-dimensional microparticle or nanoparticle having an asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c); and (b) one or more molecules capable of interacting with one or more T cell receptors (TCRs) of a T cell.

As the particle becomes flatter, the radius of curvature becomes larger. Conversely, as a surface on the particle becomes more curved, the radius of curvature becomes smaller. In some embodiments, the particle has at least one surface that has a radius of curvature that does not include the range from about 1 micron to about 10 microns.

In some embodiments, the non-spherical shape comprises a prolate ellipsoid, which is defined by the equation $a > b = c$. In other embodiments, the non-spherical shape comprises a tri-axial ellipsoid, which can be described by the equation $a > b > c$. In yet other embodiments, the non-spherical shape comprises an oblate ellipsoid, which can be described by the equation $a = b > c$. In other embodiments, the non-spherical shape has a dimension (a) along the x axis is equal to the dimension (b) along the y axis, both of which are much less than dimension (c) along the z-axis, such that $a = b \ll c$ and the three-dimensional microparticle or nanoparticle comprises a rod.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 μm). In such embodiments, the particle also can be referred to as a "microparticle". Thus, the term "microparticle" includes particles having at least one dimension in the range of about one micrometer (μm), i.e., $1 \times 10^{-6}$ meters, to about 1000 μm. The term "particle" as used herein is meant to include nanoparticles and microparticles.

As used herein, an "artificial antigen presenting cell" (aAPC) is an artificial biomimetic particle-based platform that has been made in vitro and has not been made naturally by a body.

As used herein, an "antigen presenting cell" is a cell that comprises a molecule that is capable of binding to the T cell receptor (TCR) on a T cell and has other factors which direct the T cell response. As used herein, the term "capable of" refers to having the capacity or ability, for example, a molecule that is "capable of" binding to a receptor is a molecule that has a three-dimensional structure having the capacity or ability to interact and/or bind with a receptor.

As used herein, the term "molecule" generally refers to two or more atoms held together by covalent bonds. Therefore, a molecule can be relatively small, such as the size of a peptide, or it can be relatively big, such as the size of a protein comprising several polypeptides. As used herein, a molecule is not restricted by size.

As used herein, an "antigen" is a molecule or part of a molecule that can be bound by a MHC and presented to a T cell receptor. Examples of antigens include, but are not limited to, microbial structures, such as bacterial and fungal cell walls, protozoan cell membranes, bacterial and fungal capsules, viral capsids, viral glycoproteins, microbial toxins, allergens, such as dust mites, pollen, hair, dander, bee venom, drugs, and other agents causing allergic reactions, foreign tissue or cells, and the body's own cells that the body fails to recognize as normal, such as cancer cells, infected cells, and cells involved in autoimmune diseases.

In some embodiments, the molecule is an antigen presented by the major histocompatibility complex (MHC). In some embodiments, the major histocompatibility complex is the human leukocyte antigen (HLA). In general, MHC Class II molecules mediate specific immunity to an antigen and Class I molecules mediate destruction of host cells displaying that antigen. In other embodiments, an antigen presenting cell also comprises a molecule that binds to or interacts with another receptor on a T cell.

In particular embodiments, the three-dimensional microparticle or nanoparticle comprises a prolate ellipsoid, wherein the dimension (a) along the x-axis is greater than the dimension (b) along the y-axis, and wherein the dimension (b) along the y-axis is equal to the dimension (c) along the z-axis, such that the prolate ellipsoid can be described by the equation $a > b = c$. In other embodiments, the ellipsoid is a tri-axial ellipsoid, wherein the dimension (a) along the x-axis is greater than the dimension (b) along the y-axis, and wherein the dimension (b) along the y-axis is greater than the dimension (c) along the z-axis, such that the tri-axial ellipsoid can be described by the equation $a > b > c$. In yet other embodiments, the ellipsoid is an oblate ellipsoid, wherein the dimension (a) along the x-axis is equal to the dimension (b) along the y-axis, and wherein the dimension (b) along the y-axis is greater than the dimension (c) along the z-axis, such that the oblate ellipsoid can be described by the equation a=b>c. The presently disclosed asymmetrical particles, however, do not include embodiments in which a=b=c.

In still other embodiments, the microparticle or nanoparticle has an aspect ratio ranging from about 1.1 to about 5. In other embodiments, the aspect ratio has a range from about 5 to about 10. In some embodiments, the aspect ratio has a range from about 1.5 to about 3.5, including 1.5, 2, 2.5, 3, and 3.5.

Generally, the three-dimensional microparticle or nanoparticle comprises a material having one or more of the following characteristics: (i) one or more degradable linkages; (ii) a stretchable Young's modulus ranging from $10^6$-$10^{10}$ N/m$^2$ and in some embodiments $10^7$-$10^9$ N/m$^2$; and (iii) a glass transition temperature such that the material comprising the three-dimensional microparticle or nanoparticle is a solid at room temperature and/or body temperature. The particles can also be composed of copolymers, with one or more constituents being defined as above.

As used herein, "glass transition temperature" refers to the temperature at which amorphous polymers undergo a transition from a rubbery, viscous amorphous liquid, to a brittle, glassy amorphous solid. As used herein, "Young's modulus of elasticity" quantifies the elasticity of the polymer. It is defined, for small strains, as the ratio of rate of change of stress to strain.

As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

Generally, to be biodegradable, the presently disclosed materials, e.g., microparticles and/or nanoparticles, contain a degradable linkage. Representative degradable linkages include, but are not limited to:

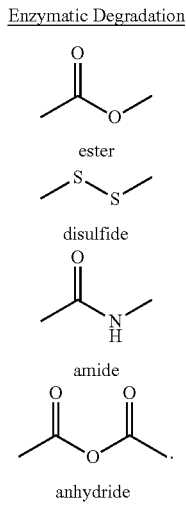

Enzymatic Degradation

In some embodiments, the three-dimensional microparticle or nanoparticle comprises a material having one or more of the following characteristics: (i) one or more degradable linkages; (ii) a stretchable modulus; and (iii) a glass transition temperature such that the material comprising the three-dimensional microparticle or nanoparticle is a solid at room temperature and/or body temperature. In other embodiments, the degradable linkage is selected from the group consisting of an ester linkage, a disulfide linkage, an amide linkage, an anhydride linkage, and a linkage susceptible to enzymatic degradation. In particular embodiments, the microparticle or nanoparticle comprises a biodegradable polymer or blends of polymers selected from the group consisting of poly(lactic-co-glycolic acid) (PLGA), poly (beta-amino ester) (PBAE), polycaprolactone (PCL), polyglycolic acid (PGA), polylactic acid (PLA), poly (acrylic acid) (PAA), poly-3-hydroxybutyrate (P3HB) and poly(hydroxybutyrate-co-hydroxyvalerate). In other embodiments, nondegradable polymers that are used in the art, such as polystyrene, are blended with a degradable polymer or polymers from above to create a copolymer system. Accordingly, in some embodiments, a nondegradable polymer is blended with the biodegradable polymer.

Other biodegradable polymers suitable for use with the presently disclosed subject matter are provided in International PCT Patent Application Publication No. WO/2010/132879 for "Multicomponent Degradable Cationic Polymers," to Green et al., published Nov. 18, 2010, which is incorporated herein by reference in its entirety.

A T cell or T lymphocyte is a cell that belongs to a group of white blood cells known as lymphocytes and plays a central role in cell-mediated immunity. Different types of T cells include, but are not limited to, T helper cells, cytotoxic T cells, memory T cells, regulatory T cells (also known as suppressor cells), and natural killer T cells. A T cell can be distinguished from other lymphocytes by the presence of a T cell receptor (TCR) on its cell surface. A T cell receptor is a protein that is found on the surface of a T cell and it is responsible for recognizing antigens bound to MHC molecules. This recognition ensures that only a T cell with a TCR specific to a particular antigen is activated. In some embodiments, the interaction of the TCR with a MHC: antigen complex is the first signal in the activation or modulation of a T cell. The antigen can be presented to the T cell by a MHC-dimer or -tetramer molecule. The MHC-dimer or -tetramer molecule can be easily loaded with any MHC-restricted peptide of interest. By loaded, it is meant that the peptide is attached in some way to the MHC-dimer or -tetramer, whether by covalent interactions or by noncovalent interactions or both.

In some embodiments, the molecule capable of interacting with the TCR is a peptide. As used herein, a "peptide" is a shorter polymer of amino acid monomers. In some cases, a peptide comprises only a few amino acids and in other embodiments, a peptide comprises hundreds of amino acids. A "polypeptide" refers to a longer polymer of amino acids, generally from about 50 amino acids to a larger protein. In general, there is overlap between the size of a peptide and a polypeptide. In some embodiments, peptides interacting with MHC Class II molecules are typically 13 to 17 amino acids in length, and in other embodiments, shorter or longer peptides are common and allowed. In still other embodiments, peptides interacting with MHC Class I molecules have more stringent requirements of generally less than 15 amino acids length.

In other embodiments, the peptide is loaded onto a MHC-Ig molecule or a HLA:Ig molecule before interacting with the TCR. In some embodiments, the HLA:Ig molecule is a HLA:A2:Ig molecule.

In some embodiments, a second signal is required for T cell activation or modulation. This second signal may be another receptor on the T cell that acts to costimulate the T cell. Examples of receptors include, but are not limited to CD28 (Accession Nos. NP_006130, NP_001230006, NP_001230007), CD2 (Accession No. NP_001758), CD5 (Accession No. NP_055022), CD30 (Accession No. NP_001235), OX40 (NP_003318), 4-1BBL (Accession No. NP_001070977), ICAM-1 (Accession No. NP_000192) and LFA-1 (NP_002200), for example. Accession numbers are given only as examples and similar proteins with other accession numbers also may be used in the presently disclosed subject matter.

A "CD28 receptor" is a protein found on the surface of a T cell. It is activated or induced by stimuli, such as products of pathogens and breakdown products of cells, via the B7 protein. In some embodiments, the CD28 receptor is involved in the second signal required for T cell activation or modulation.

A "B7 protein" is a peripheral membrane protein that when paired with the CD28 receptor on a T cell, enhances or decreases the signal from the interaction of the TCR with the MHC: antigen complex on a T cell. The B7 protein comprises the CD80 (or B7.1) protein and the CD86 protein (or B7.2).

As used herein, the MHC: antigen complex, the Ig molecule, the B7 protein, the anti-CD3 molecule, and any other molecule comprising the aAPC may constitute the whole molecule, protein, or complex or it may constitute the domain of the molecule, protein, or complex that is involved in binding or interacting with the T cell. In other words, in some embodiments, the aAPC of the presently disclosed subject matter can comprise only the part of the molecule, protein, or complex that interacts with the T cell. For example, an aAPC comprising the B7 protein may comprise a full length B7 protein, only one polypeptide of the B7 protein, or only the CD28 receptor binding domain of the B7 protein.

In some embodiments, the T cell is modulated by costimulation of both the TCR and one of the other receptors on a T cell. In some embodiments, costimulation of both the TCR and one of the other receptors results in activation of the T cell, while in other embodiments, costimulation of both the TCR and one of the other receptors results in a decrease in activation of the T cell. Modulation can include activation, inactivation, and other forms of altered cell function.

Accordingly, in some embodiments, the aAPC further comprises a molecule capable of interacting with a receptor other than a TCR on the T cell. In some embodiments, the receptor other than a TCR on the T cell is selected from the group consisting of CD28, CD2, CD5, CD44, OX40, 4-1BBL, ICAM-1, and LFA-1. In particular embodiments, the receptor other than a TCR on the T cell is CD28. In some cases, the CD28 receptor interacts with an anti-CD28 antibody or a B7 protein.

The aAPC can further comprise a drug or therapeutic agent. In some embodiments, the drug or therapeutic agent is a protein. As used herein, a "drug" is a substance that has a physiological effect when introduced into a subject. A drug also can be tested in vitro, for example, in cell culture, to determine its effect on a cell. A "protein drug" is a drug comprising a peptide(s) or polypeptide(s).

In other embodiments, the aAPC further comprises at least one peptide or protein on one or more surfaces of the aAPC and/or within the aAPC.

The presently disclosed subject matter also provides kits comprising the aAPC. In general, the kits comprise aAPCs in an amount sufficient to treat at least one patient at least one time to modulate T cells in the patient. Typically, the aAPCs of the kit will be supplied in one or more container, each container containing a sufficient amount of particles for at least one dosing of the patient.

Figure 18A:
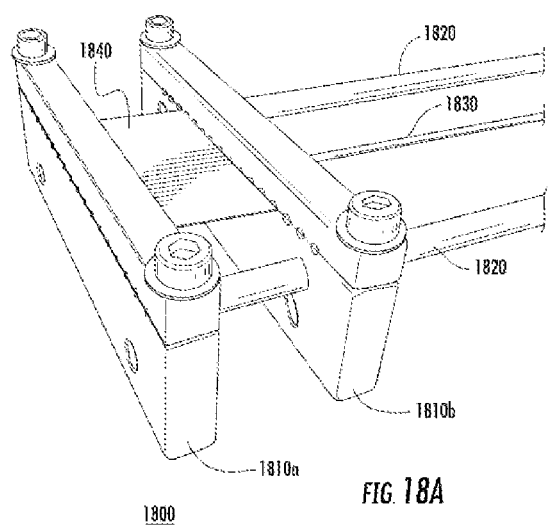
Figure 18B:
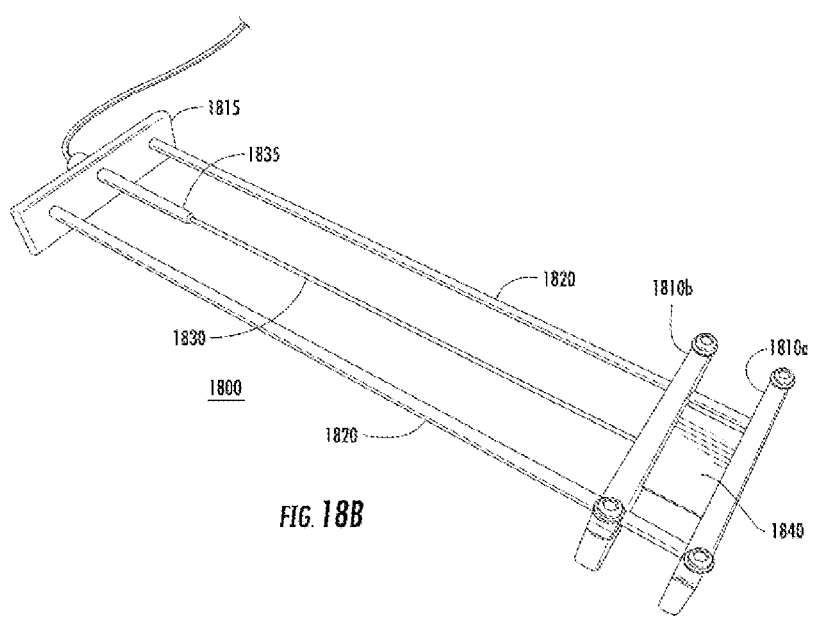

In other embodiments, the presently disclosed subject matter includes a kit comprising the raw materials for making the presently disclosed aAPCs and the presently disclosed device for stretching the particles (see FIGS. 18A and 18B).

The aAPCs of the presently disclosed subject matter can be used to modulate T cells in many different applications. For example, the aAPCs can be used to study the CD8+ T cell response to influenza epitopes in vitro (Lee et al., 2011) and also can be used in methods of preventing and/or treating patients for influenza in vivo. As another example, these aAPCs, such as HLA-A2-Ig-based aAPCs, can be used to stimulate CD8(+) T cells using antigens specific for influenza and measles (Ndhlovu et al., 2010).

As a further example, compositions and methods of the presently disclosed subject matter can use aAPCs to study, prevent, or treat autoimmune diseases, such as Type 1 diabetes mellitus (T1D). In the case of T1D, one potential target is the Fas ligand (FasL) (Xiao et al., 2011).

As still another example, an aAPC based system can be used for ex vivo expansion of human cytomegalovirus specific cytotoxic T lymphocytes for adoptive immunotherapy (Chiu et al., 2011).

As another example, the aAPC based system can be used in a novel cellular microarray assay utilizing soluble peptide-loaded HLA-A2-Ig dimer complexes that optimizes the avidity of peptide-HLA binding by preserving the molecular flexibility of the dimer complex while attaining much higher concentrations of the complex relative to cognate T cell receptors. This high-throughput broad-based assay enables the use of cellular microarrays to determine the stability and flux of antigen-specific T cell responses within and across populations (Li et al., 2011).

Further, the aAPCs can be used to deplete allo- or antigen-specific T cells, such as by taking advantage of the Fas/Fas ligand signaling pathway to efficiently induce antigen-presenting cell-mediated apoptosis in targeted T cells (Scheutz et al., 2010).

Also, aAPCs made by covalently coupling (pep)MHC-Ig dimers and B7.1-Ig molecules to magnetic beads can be used to improve immunotherapy efficacy by rescuing antitumor activity of low-avidity tumor-specific cytotoxic T lymphocytes (Ugel et al., 2009).

In addition, killer artificial APCs (kappaaAPCs) can be generated by coupling an apoptosis-inducing alpha-Fas (CD95) IgM mAb together with HLA-A2 Ig molecules onto beads. These kappaaAPCs deplete targeted antigen-specific T cells in a Fas/Fas ligand (FasL)-dependent fashion and therefore have potential for use in treatment of autoimmune diseases and allograft rejection (Schuetz et al., 2008).

As another example, natural killer T (NKT) cells play a pivotal role in maintaining immune homostasis. They recognize lipid antigen in the context of CD1d molecules and subsequently produce cytokines that activate cells of both the innate and adaptive immune responses. Many studies examining patients with autoimmune disease or cancer have shown that there is a reduction in both NKT cell number and function. The aAPC system can facilitate the growth and analysis of NKT cells through the use of CD1d-expressing aAPC. CD1d-based aAPC can effectively propagate both canonical (iNKT cells) and noncanonical (Valpha 14(−)) NKT cells. Importantly, CD1d-Ig aAPC can expand NKT cells from cancer patients and can be used as a novel tool in adoptive immunotherapeutic strategies (Webb et al., 2009)

The aAPCs can also be used in providing a sensitive and specific assay for evaluation of immune responses. Cellular immune responses are often not analyzed because of technical hurdles and the volume of blood required. Therefore, a sensitive and specific assay for antigen-specific T cells that utilizes a small volume of blood would facilitate new vaccine evaluation. An assay for quantifying virus-specific CD8(+) T cells can combine the use of HLA-A2 immuno-globulin-based aAPCs for stimulation of antigen-specific CD8(+) T cells in whole blood with quantitative real-time reverse transcription-PCR (qRT-PCR) to detect gamma interferon (IFN-gamma) mRNA (Ndhlovu et al. 2009). This assay is able to analyze the CD8(+) T cell responses to a wide variety of antigens.

As another example, natural killer T (NKT) cells recognize lipid antigen presented by CD1 molecules. NKT cells can both directly, through cytotoxicity, and indirectly, through activation of other effector cells, mediate antitumor immunity. It has been shown, however, that tumor-associated lipids are frequently shed into the tumor microenvironment, which can mediate immunosuppressive activity. For example, given that ovarian cancer-associated ascites has been reported to have increased levels of gangliosides, the effect of tumor-associated and other ascites on CD1d-mediated antigen presentation to NKT cells can be examined using aAPCs (Webb et al., 2008).

As a further example, adoptive immunotherapy for treatment of cancers and infectious diseases is often hampered by a high degree of variability in the final T cell product and in the limited in vivo function and survival of ex vivo expanded antigen-specific cytotoxic T cells. It has been found that HLA-Ig based aAPC stimulated tumor-specific CTL from human peripheral blood T lymphocytes showed robust expansion and functional activity, such as in a human/SCID mouse melanoma model (Durai et al., 2008). Therefore, therapeutic in vivo activity of HLA-Ig based aAPC expanded CTL can be used to control tumor growth.

As still another example, lipid overload, associated with metabolic disorders, occurs when fatty acids accumulate in non-adipose tissues. Cells of these tissues use major histocompatibility complex (MHC) class I molecules to present antigen to T cells in order to eliminate pathogens. As obesity is associated with impaired immune responses, aAPCs can be used to study the early stages of lipid overload and antigen presentation by treating aAPCs with either the saturated palmitic acid (PA), abundant in the high fat Western diet, or the monounsaturated oleic acid (OA), a component of the Mediterranean diet, for example, and looking at immunity by the effect on MHC I-mediated antigen presentation (Shaikh et al., 2008).

II. METHODS FOR USING ARTIFICIAL ANTIGEN PRESENTING CELLS

In some embodiments, the presently disclosed subject matter provides a method for modulating a T cell, the method comprising (a) providing an artificial antigen presenting cell (aAPC) comprising: (i) a three-dimensional microparticle or nanoparticle having an asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c); and (ii) one or more molecules capable of interacting with one or more T cell receptors (TCRs) of a T cell and one or more molecules capable of interacting with a receptor other than a TCR on the T cell to costimulate the T cell; (b) contacting the T cell with the aAPC; and (c) allowing the T cell to be modulated.

As used herein, "contacting" or "interacting" means any action that results in at least one molecule affecting another molecule, either by physically contacting, or by getting in close enough proximity that one molecule affects the actions of another molecule. For example, the TCR of a T cell may interact with a MHC: antigen complex in such a way that the antigen of the MHC: antigen complex activates the T cell without physically binding to the TCR. In another example, the antigen physically contacts the TCR.

The method can be practiced in vivo, in which case contacting means exposing at least one T cell in a subject to at least one aAPC. According to the presently disclosed subject matter, contacting includes exposing at least one T cell to at least one aAPC, such as, for example, by administering at least one dose of aAPC to a subject via any suitable route. It also may comprise exposing cells in vitro or ex vivo by introducing, and preferably mixing, at least one aAPC and at least one T cell in a controlled environment, such as in a cell culture dish or a tube. According to the presently disclosed subject matter, contacting includes introducing, exposing, and the like, at least one aAPC at a site distant from the cells to be contacted, and allowing the bodily functions of the subject, or natural (e.g., diffusion) or human-induced (e.g., swirling) movements of fluids to result in contact of the aAPC(s) and the T cell(s). Where practiced ex vivo, the cells also may be re-introduced into a subject, preferably the subject from whom they were obtained.

The aAPCs may be used for multiple manners of T cell modulation including T cell activation and T cell inactivation/inhibition.

T cell activation and/or modulation refers to the engagement of both the T cell receptor and another receptor on the T cell. In the absence of costimulation by another receptor, T cell receptor signaling alone results in anergy, a state in which the T cell cannot activate an effective immune response. Anergy, however, may be taken advantage of for therapeutic uses. For example, the immune response to grafting of transplanted tissue and organs can be minimized without weakening the entire immune system. As another example, anergy may be used to induce activated lymphocytes to become unresponsive with autoimmune diseases, such as diabetes, mellitus, multiple sclerosis, and rheumatoid arthritis.

Effective T cell activation, which means that both the TCR and another receptor that provides costimulation are stimulated, results in a cascade of events resulting in clonal expansion or proliferation of the T cell to increase the number of T cells capable of binding to the specific antigen. "Clonal expansion", "T cell proliferation" and "T cell expansion" are used interchangeably herein.

In some embodiments, the molecule capable of interacting with the TCR is a peptide. In other embodiments, the peptide is loaded onto a MHC-Ig molecule or a HLA:Ig molecule before interacting with the TCR.

In some embodiments, the receptor other than a TCR on the T cell is selected from the group consisting of CD28, CD2, CD5, CD44, OX40, 4-1BBL, ICAM-1, and LFA-1. In other embodiments, the receptor other than a TCR on the T cell is CD28. In still other embodiments, the CD28 receptor interacts with an anti-CD28 antibody or the B7 protein.

In some embodiments, the T cell used in the methods is a naïve T cell. A "naïve T cell" is a T cell that can respond to a novel pathogen that the immune system has not yet encountered. Recognition by a naïve T cell of its cognate antigen results in the initiation of an immune response. In other embodiments, modulation of the T cell results in proliferation of the T cell.

The methods for using an aAPC of the presently disclosed subject matter can be in vitro, in vivo, or ex vivo. In some embodiments, contacting occurs in a subject, such as in a human or in a non-human animal. In other embodiments, contacting comprises administering to the subject one or more doses of aAPCs in an amount sufficient to treat a disease, disorder, or dysfunction. A disease, disorder, or dysfunction refers to any condition that affects the health of a subject. As the presently disclosed subject matter affects T cells which are a central part of the immune response, methods and compositions of the presently disclosed subject matter will affect a wide variety of diseases, disorders, or dysfunctions. Examples include cancer and infectious diseases, which may be treated by an increased immune response. Other examples include autoimmune diseases, allergies, and transplanted tissue that may be treated by an attenuated immune response. The presently disclosed subject methods and compositions may be modified to treat a particular disease, disorder, or dysfunction.

Administering may be by oral ingestion, through injection, by infusion, through topical administration, through inhalation, through sublingual absorption, through rectal or vaginal delivery, subcutaneously, and combinations thereof. In some embodiments, the disease, disorder, or dysfunction is cancer or an infectious disease. In other embodiments, the method is an ex vivo method comprising removing at least one T cell from the subject, contacting the at least one T cell with at least one aAPC, and returning the T cell to the subject. In still other embodiments, the in vitro method occurs in cell culture.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like. As used herein, a "dose" refers to the amount of aAPCs administered to a subject that is sufficient to treat the subject for a disease, disorder, or dysfunction.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

III. METHODS FOR PREPARING ARTIFICIAL ANTIGEN PRESENTING CELLS

The presently disclosed subject matter also provides methods for preparing an aAPC. In some embodiments, the method is a method for making an artificial antigen presenting cell (aAPC) comprising a three-dimensional microparticle or nanoparticle having asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c); and one or more molecules capable of interacting with one or more T cell receptors (TCRs) of a T cell, the method comprising (a) providing or preparing a plurality of microparticles or nanoparticles; (b) preparing a film comprising the plurality of microparticles or nanoparticles; (c) stretching the film comprising the plurality of microparticles or nanoparticles to form a plurality of three-dimensional microparticles or nanoparticles having an asymmetrical shape; (d) harvesting the plurality of three-dimensional microparticles or nanoparticles having an asymmetrical shape; and (e) coupling to the plurality of three-dimensional microparticles or nanoparticles having an asymmetrical shape one or more molecules capable of interacting with one or more T cell receptors (TCRs) of a T cell. In some embodiments, the film is heated before being stretched.

In other embodiments, hyper-dense ligand coated particles that have a surface density greater than what has currently been achieved can be formed. These particles can be formed by stretching microparticles or nanoparticles into an asymmetrical shape, adding the functional ligands to the particles, and then allowing the particles to relax back partially or completely to the original spherical shape. For example, a plurality of three-dimensional microparticles or nanoparticles can be relaxed back partially or completely to a spherical or near spherical shape. In the case of an ellipsoid, the parameters (a), (b), or (c) are approximately equal in a "near spherical shape."

The reaction scheme for one embodiment of these methods is shown in FIG. 17. In Step (1), a SH-PEG-NH2 molecule is added to maleimide activated streptavidin to form a Streptavidin-PEG-NH2 molecule. Step (2) involves the addition of biotinylated peptides/antibodies/HLA-Ig dimer to streptavidin-PEG-NH2. In Step (3), the PEG part of the molecule is conjugated to elliptical disk PLGA or another COOH terminated polymer using EDC. Finally, the temperature is raised to lower the aspect ratio of the elliptical disk to relax it back partially or completely to a spherical shape. This "hyper-dense" ligand coated particle has more ligands on its surface because the particle was functionalized while it was stretched. This method can be performed on a wide variety of particles and ligands. Conversion back to or partially to a spherical state after stretching can be performed using heat, chemicals, and any other method that will allow the particle to relax to a previous state.

Accordingly, in some embodiments, the presently disclosed methods comprise a method wherein a plurality of three-dimensional microparticles or nanoparticles is relaxed back partially or completely to a spherical shape. In some embodiments, relaxing occurs by the addition of heat. In some embodiments, relaxing occurs by the addition of heat. In other embodiments, chemicals can be added to the plurality of particles to allow the particles to resume their partial or complete original shape.

IV. DEVICE FOR STRETCHING A FILM

In yet other embodiments, the presently disclosed subject matter provides a device for stretching a film, the device comprising: at least a first and a second block adapted to immobilize at least two edges of a film, the at least first and second blocks comprising one or more surfaces in contact with the film; the at least first and second blocks positioned parallel to one another and perpendicular and in operational communication with at least two parallel rods, wherein at least the second block is adapted to be selectively positioned along the at least two parallel rods relative to the first block; the device further comprising one or more of (i) a cord attached to the second block and (ii) a screw attached to the cord, each of which is adapted to selectively position the second block along the at least two parallel rods relative to the first block.

In some embodiments, the device further comprises one or more cushings in operational communication with the at least two parallel rods. In yet other embodiments of the presently disclosed device, the first and the second block comprise at least one patterned face to facilitate immobilizing the at least two edges of the film. In other embodiments, the at least first and second blocks further comprise one or more rubber pads in operational communication with the one or more surfaces in contact with the film.

V. DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Microparticle Fabrication

The poly(lactide-glycolide) (PLGA) microparticles were made by dissolving 200 mg of acid-terminated PLGA (50:50 LA/GA, MW 38,000-54,000, Sigma-Aldrich) in 5 ml of dicholoromethane (ACS grade, Sigma-Aldrich). The dissolved PLGA was then added dropwise to 50 mL of an ice-cold 1% poly(vinyl alcohol) (PVA) solution, which was homogenized at 5,000 rpm. After dropwise addition, the solution was allowed to homogenize for an additional minute, and then added to a 100 mL solution of 0.5% PVA, which was stirring at 500 rpm in the cold room (at 4° C.). After stirring for 4 hours to allow for solvent evaporation, the particles were centrifuged (4000 rpm for 5 min) and washed 3×, resuspended in 0.5 mL of deionized water and lyophilized.

Example 2

Film Formation and Particle Stretching

Lyophilized microparticles were added to a solution containing 10% PVA and 2% glycerol by weight at 5 mg/mL (particles/mL solution). Then the film was poured on a leveling table and allowed to dry in a chemical hood overnight. After overnight drying at room temp, strips of the film were cut out and placed on a stretching device consisting of two blocks that can be separated by sliding on rods or by pulling on a cord (see FIGS. 18A-18D).

Referring now to FIGS. 18A-18D is a representative stretching device 1800. Particles cast into film 1840 (as described immediately hereinabove) are stretched by heating film 1840 and separating blocks 1810a and 1810b. Stretching device 1800 also includes block 1815. In some embodiments, blocks 1810a, 1810b, and 1815 are fabricated from aluminum. Blocks 1810a and 1810b slide on rods 1820 by physically pulling them apart or by pulling on cord 1830 or twisting screw 1835, which in turn pulls on cord 1830. In some embodiments, rods 1820 are fabricated from aluminum.

In some embodiments, stretching device 1800 includes cushings (element A in FIG. 18C) to allow block 1810b to slide smoothly along rods 1820 and reduce friction. In some embodiments, the cushings are fabricated from plastic. In some embodiments, stretching device 1800 includes patterned clamp faces (element B in FIG. 18C) to improve grip on film 1840 and reduce slippage. In some embodiments, stretching device 1800 includes rubber padding (element C in FIG. 18C) to distribute pressure and prevent tearing of film 1840.

Figure 18C:
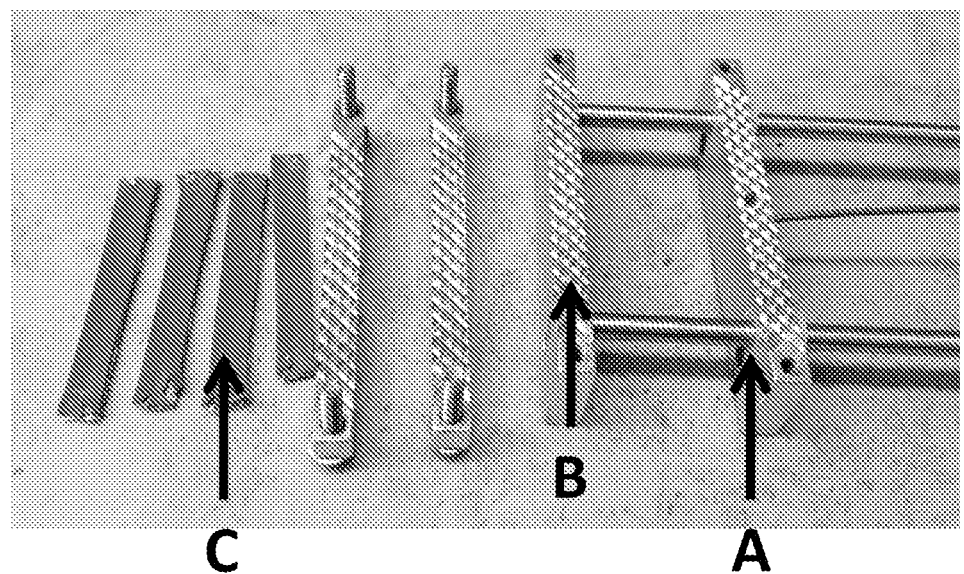
Figure 18D:
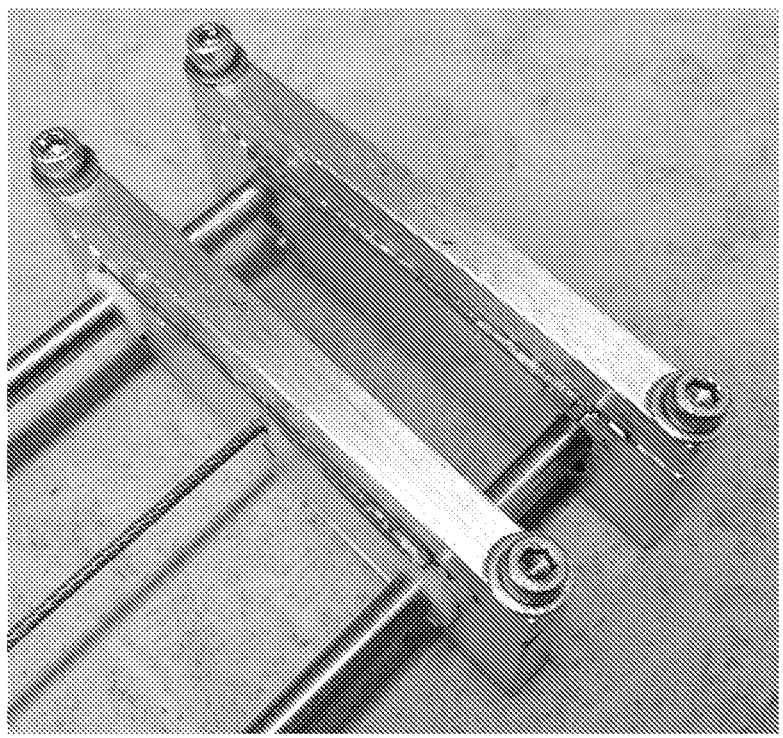

Stretching device 1800 when fully assembled with the additional elements A-C shown in FIG. 18C can be seen in FIG. 18D.

Stretching device 1800 as depicted in FIGS. 18A-18D can be used to stretch films in one dimension. One of ordinary skill in the art would recognize that additional blocks and rods could be added to stretching device 1800 to allow stretching of films in other dimensions, as well.

In representative embodiments, the film and custom-made stretcher were placed in a 90° C. oven for 10 minutes and then the film was slowly stretched inside of the oven to the desired stretch ratio by separating the two blocks. After stretching, the film was allowed to cool down to room temperature. The stretched section was cut out of the film and dissolved in 10 mL of deionized water, then centrifuged (4000 rpm for 5 min) and washed 3×, and finally resuspended in 200 µL of deionized water and lyophilized. "Non-stretched" particles also are prepared in the same way—they were heated alongside of the stretched particles, but simply not stretched.

Example 3

Preparation of MHC-Ig Dimers

Soluble MHC-Ig dimers were prepared and loaded with peptide as described. Schneck, J. P., J. E. Slansky, S. M. O'Herrin, and T. F. Greten. 2001. Monitoring antigen-specific T cells using MHC-Ig dimers. Current protocols in immunology/edited by John E. Coligan . . . [et al.]. Chapter 17: Unit 17.2.

Briefly, Db-Ig molecules were stripped under mildly acidic conditions (pH 6.5) and refolded in the presence of 40-fold molar excess peptide and 2-fold molar excess of human β2-microglobulin. Peptides GP100 (KVPRNQDWL; the "cognate" peptide) and ASN (ASNENMETH; a "non-cognate" peptide) were purchased from Genscript (Piscataway, N.J.). Protein concentration was determined after labeling by size exclusion High Performance Liquid Chromatography.

Example 4 aAPC Synthesis

Stretched and non-stretched microparticles were resuspended in coupling buffer (0.1M MES pH 6.0), and activated with EDC (1-Ethyl-3-(3-dimethylaminopropyl)carbodiimide, Sigma-Aldrich) and sulfo-NHS (N-hydroxysulfosuccinimide). As a representative example, 5 mg of microparticles were resuspended in 1 mL of coupling buffer and activated with 10 mg of EDC and 13 mg of sulfo-NHS for 15 min at 1000 rpm on a multitube vortexer (VWR). Activated microparticles were then centrifuged, the supernatant was removed, and the aAPCs were resuspended in 1 mL PBS (pH 7.4) and transferred to a 5 mL glass scintillation vial for coupling. After addition of protein (bivalent cognate (+) or non-cognate (−) peptide-in-MHC and anti-CD28 antibody), the reaction was allowed to proceed in the cold room (4° C.) for 4 hours. After 4 hours, the aAPCs were centrifuged and washed 2× with PBS, then centrifuged again and re-suspended in 200 µL of 0.2 µm-filtered sterilized 90-mg/mL endotoxin-free sucrose solution, frozen, and lyophilized overnight.

Example 5

Characterization of aAPCs

Measuring Size and Aspect Ratio by SEM

Lyophilized particle samples were spread on conductive carbon tape mounted on aluminum SEM mounts (Electron Microscopy Sciences, Hatfield, Pa.). Samples were sputter coated with a chromium sputter coater and imaged on a Leo/Zeiss Field emission SEM in the Johns Hopkins Core Microscopy facility. Particle size and aspect was quantified using ImageJ software. For spherical particles, a single diameter was measured for each particle. For non-spherical particles, two diameters were measured (long-axis and short-axis) and the aspect ratio was calculated by dividing the two.

Surface Protein Quantification and Release

Surface protein quantification was performed by conjugation of unlabeled anti-CD28 mAb and fluorescently labeled MHC-IgG dimer to the surface of pre-activated 2-fold stretched or spherical PLGA microparticles for 4 hours at 4° C. These aAPC were centrifuged washed 3×, and then their fluorescence was characterized on a Synergy 2 plate reader (Biotek, Winooski, Vt.). Release from surface was characterized by incubating 10 mg of aAPC (stretched, non-stretched) with labeled dimer in 500 µL PBS at 37° C. for 1 week. At 3 days and 7 days, the particles were centrifuged and the supernatant was removed and stored for subsequent analysis. At 7 days, the supernatant was removed, the particles were resuspended, and the fluorescence was characterized.

Intracellular Cytokine Staining

Six days after primary stimulation with aAPC, T cell functional activity was assessed by re-challenge with peptide-pulsed C57Bl/6j splenocytes. Splenocytes were pulsed with the indicated concentration of peptide for 2 hours at 37° C. and then washed. 200,000 aAPC-activated T cells were incubated in complete RPMI with 200,000 splenocytes for 4 hours in a round bottom 96-well plate in the presence of 0.2-µL GolgiPlug, 0.2 µL GolgiStop, and anti-CD107a-fitC (BD Biosciences, Mountain View, Calif.). Cells were washed and fixed using a BD Cytofix/Cytoperm kit (BD Biosciences) according to the manufacturer's instructions, then stained with anti-IFNγ PE (BioLegend). Cytokine staining was assessed by flow cytometry and frequency of cytokine functional cells was assessed by comparison with an unstimulated control in FlowJo (TreeStar).

aAPC-T Cell Conjugate Formation Evaluation

PLGA microparticles, with encapsulated 5(6)-carboxy-tetramethylrhodamine dye (TAMRA, Nova Biochem, San Diego, Calif.), were synthesized for confocal imaging. The TAMRA was dissolved in dichloromethane at 1 mg/mL. 200 mg of acid-terminated PLGA was dissolved in 4.9 mL of DCM and 100 µL of TAMRA solution was added to the PLGA DCM phase. Particle synthesis otherwise followed the same protocol as the single emulsion particles above. These labeled particles were then cast into a film, and the film stretching and subsequent synthesis of aAPC from stretched and non-stretched TAMRA-loaded particles was accomplished as before. $1 \times 10^6$ CFSE-labeled T cells were incubated with 1 mg stretched or non-stretched aAPC for 60 minutes at 37° C. in a No. 1.5 glass bottom dish (MatTek, Ashland, Mass.). Images were acquired on a Zeiss LSM 510 META (Zeiss, Oberkochen, Germany) laser scanning confocal at 40× magnification at the Johns Hopkins School of Medicine Microscopy Facility.

In Vivo Activity of aAPCs

A subcutaneous B16 melanoma tumor prevention mouse model (FIG. 9a) was developed. The animals were preinjected intravenously (i.v.) with naïve pmel T cells (day −1, $2 \times 10^6$ cells/animal), subcutaneously (s.c.) in the flank with particles (day 0, 2 mg particles/animal), then injected with 200,000 tumor cells in the hindlimb (day 3). Responses were boosted with subsequent s.c. injection of a second particle batch (day 6, 2 mg particles/animal), and tumor growth over the course of the experiment was followed by measurement with external calipers. Once the tumor size reached 200 cm², the mice were sacrificed. Treatment groups consisted of stretched and non-stretched cognate aAPC (n=8), and control groups consisted of stretched non-cognate (n=8) and T cell alone groups (n=5). Statistics for tumor size presented in FIG. 9b were performed by 1-way ANOVA with Tukey post test. Statistics for survival analysis presented in FIG. 9c were performed using the Log-rank (Mantel-Cox) test.

Example 6

In Vitro CTL Induction and CFSE Dilution

T cells used were obtained from homogenized mouse spleens after depletion of RBC by hypotonic lysis. Cytotoxic lymphocytes were isolated using a CD8 negative isolation kit and magnetic enrichment column from Miltenyi Biotec (Cologne, Germany) and if necessary labeled with Carboxyfluorescein succinimidyl ester (CFSE) for 15 minutes at 37° C., then washed extensively. Cells and particles at the indicated amounts and dosages were mixed and cultured for 4-7 days in complete RPMI media supplemented with T cell factor, a cytokine cocktail harvested from human plasma. Durai, M., et al., In vivo functional efficacy of tumor-specific T cells expanded using HLA-Ig based artificial antigen presenting cells (aAPC). Cancer immunology, immunotherapy: CII. 58: 209-20 (2009). Cell proliferation was quantified by manual cell counting, and final T cell count was divided by the initial T cell count for fold-change data.

Example 7

Supplemental Calculations

Determining the Lengths of a, b, c

For a spheroid that has been elongated in one dimension, since total volume is conserved from a sphere, the length of the short axes is related to the length of the long axis by $b=c=1/\sqrt{a}$. The identities of a, b, c, 1, and 2 are illustrated in FIG. 16.

Surface Area of a Prolate Spheroid

Since the geometrical shape corresponds to a prolate spheroid (a>b=c), the surface area of the spheroid can be determined by the following formula, Weisstein, E. W. Prolate Spheroid. in *MathWorld—A Wolfram Web Resource* (2012):

$$SA = 2\pi b^2 + 2\pi \frac{ab}{e}\sin^{-1}e \text{ where } e = \sqrt{1 - \frac{b^2}{a^2}}.$$

This surface area was then normalized by the surface area of a sphere with radius 1.

Equivalent Protein Density

Equivalent protein density with total protein content held constant is the inverse of the normalized surface area (Density =1/SA).

Radius of Curvature

The radius of curvature is the radius of a circle with the same curvature as the observed curve at that point. Thus, for flatter curves, the radius of curvature increases, as that flatness requires a larger circle to describe it.

The shape extremes of an oblate ellipsoid, also referred to as an oblate spheroid, are the equatorial radius, or semi-major axis, a, and the polar radius, or semi-minor axis, b. An ellipse can be described parametrically by:

$$x(t) = a\cos(t)$$
$$y(t) = b\sin(t)$$

For any parameterized equation of the form $$x = x(t)$$
$$y = y(t),$$

the radius of curvature can be calculated from $$R = \frac{((x')^2 + (y')^2)^{3/2}}{|x'y'' - y'x''|},$$

where $$x' = dx/dt$$
$$x'' = d^2x/dt^2$$

and $$y' = dy/dt$$
$$y'' = d^2y/dt^2.$$

So for an ellipse:

$$R = \frac{(a^2\sin^2(t) + b^2\cos^2(t))^{3/2}}{ab\sin^2(t) + ab\cos^2(t)} = \frac{(a^2\sin^2(t) + b^2\cos^2(t))^{3/2}}{ab}.$$

See Weisstein, E. W. Radius of Curvature, in *MathWorld—A Wolfram Web Resource* (2012).

To calculate the radius of curvature at the tip, since t=0 corresponds to point 1 (FIG. 16), $R_a$ can be calculated using a and b as the two axes of the ellipse. To calculate the radius of curvature at the tip, since t=π/2 corresponds to point 2 (FIG. 16), $R_b$ can be calculated using a and b as the two axes of the ellipse and plugging in the variable t=π/2. Thus, $$R_a = \frac{b^3}{ab} = \frac{b^2}{a}$$

$$R_b = \frac{a^3}{ab} = \frac{a^2}{b}$$

Because the bc plane at 2 is already described by a circle, $R_c$=b=c.

Example 8

Results and Discussion

Non-Spherical aAPC Synthesis and Characterization

FIG. 2a shows a schematic of an aAPC comprising a spherical particle. In a representative, non-limiting embodiment, non-spherical, biodegradable aAPCs were synthesized by first fabricating PLGA microparticles, which were then stretched into ellipsoids using a film stretching method (FIGS. 2b and 2c). Yoo, J. W. & Mitragotri, S. Polymer particles that switch shape in response to a stimulus. *Proc Natl Acad Sci USA* 107, 11205-11210 (2010). This method offers the advantage of allowing a direct comparison of particle shape and surface area, while retaining equivalent volumes. FIG. 2d shows the interaction between a T cell and an antigen presenting cell.

The single emulsion PLGA (50:50 LA/GA, MW 38,000-54,000) microparticle synthesis resulted in spherical microparticles (FIG. 2e) with a number-weighted average diameter of 4.3 μm and a volume-weighted diameter of 6.7 μm (FIG. 2f). The aspect ratio (AR) of ellipsoidal microparticles could be controlled with a high degree of accuracy by imposing different degrees of stretch (STR) onto the film. This technique exhibits a high correlation between predicted AR and empirically measured AR (by SEM) for a fixed volume ellipsoid that has been elongated in one direction (AR = $STR^{1.5}$) (FIG. 2g). This observation indicates that particle stretching is a feasible, controllable process that allows for flexibility in specifying the shape of the resulting particles.

Figure 10:
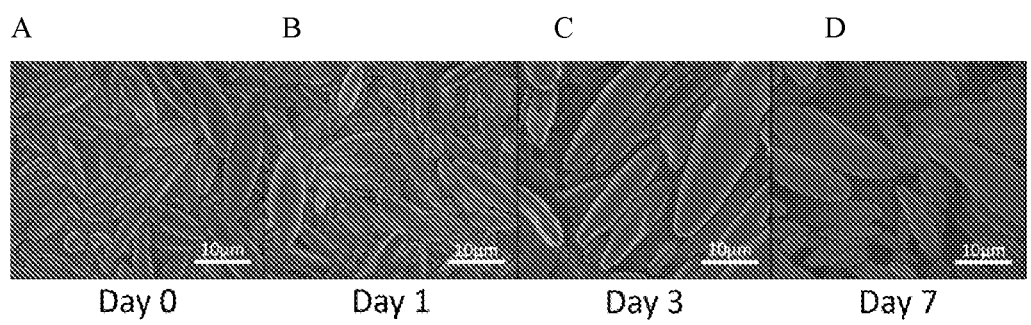

The stability of the non-spherical aAPC particle shape was characterized by analyzing their relaxation rate to the more stable spherical shape. Previous studies have indicated that relaxation rates depend on surface characteristics, molecular weight, polymer composition, and temperature. Yoo, J. W. & Mitragotri, S. Polymer particles that switch shape in response to a stimulus. *Proc Natl Acad Sci USA* 107, 11205-11210 (2010). Very little shape relaxation was observed for aAPCs fabricated from high aspect ratio particles over one week at 37° C. in PBS, indicating that the shape transition is very slow for non-spherical aAPCs with the chosen lactide to glycolide ratio (FIG. 10). This observation agrees with published relaxation timescales for high aspect ratio PLGA with hydrophilic surfaces, such as those disclosed here. Yoo, J. W. & Mitragotri, S. Polymer particles that switch shape in response to a stimulus. *Proc Natl Acad Sci USA* 107, 11205-11210 (2010).

Non-stretched and stretched microparticles were made into aAPCs by EDC-sulfo-NHS mediated covalent coupling of a dimeric MHC-Ig fusion protein, Schneck, J. P., J. E. Slansky, S. M. O'Herrin, and T. F. Greten. 2001. Monitoring antigen-specific T cells using MHC-Ig dimers. Current protocols in immunology/edited by John E. Coligan . . . [et al.]. Chapter 17: Unit 17.2, and an activating against CD28 to free carboxyl groups on the particle surface. For characterization experiments, fluorescently labeled MHC-Ig was used and total protein content for a given quantity of PLGA was assessed by fluorimetry (FIG. 2h). PLGA microparticles did not auto-fluoresce or interfere with dye emission (FIG. 11). By increasing the amount of MHC-Ig used during synthesis, protein coupling of up to 8 μg MHC-Ig/mg PLGA was achieved. At each of the protein titrations, approximately 20% coupling efficiency was achieved and final protein content depended linearly with the amount of MHC-Ig used during synthesis (FIG. 2h). In addition, no significant difference was observed between non-stretched and stretched microparticles with respect to the total protein on the surface.

While bulk polymer degradation from PLGA microparticles have been well investigated in the drug delivery field, Rothstein, S. N., et al., A unified mathematical model for the prediction of controlled release from surface and bulk eroding polymer matrices. *Biomaterials* 30, 1657-1664 (2009); Batycky, R. P., et al., A theoretical model of erosion and macromolecular drug release from biodegrading microspheres. *J Pharm Sci* 86, 1464-1477 (1997); von Burkersroda, F., et al., Why degradable polymers undergo surface erosion or bulk erosion. *Biomaterials* 23, 4221-4231 (2002), the effect of degradation on release of surface-coupled proteins is less well studied. For aAPCs, presentation of immobilized protein is critical for T cell activation and thus it is important to study release of surface immobilized proteins. Mescher, M. F., Surface contact requirements for activation of cytotoxic T lymphocytes. *J Immunol* 149, 2402-2405 (1992). To characterize surface degradation, particles bearing fluorescently labeled MHC-Ig were incubated for varying amounts of time at 37° C. Supernatants were recovered through centrifugation of the microparticles and released protein was quantified by protein fluorescence. For both spherical aAPCs and non-spherical aAPCs, 60-70% of the protein that was conjugated to the surface was released, with 30-40% remaining on the surface of the aAPCs (FIG. 2i). The release profile was not significantly different between stretched and non-stretched aAPCs.

High Aspect Ratio aAPCs Efficiently Induce T Cell Proliferation

To assess the impact of particle elongation, the ability of aAPC to induce antigen specific T cell expansion of pMEL TCR transgenic T cells was measured. Non-stretched and 2-fold stretched (AR=2.8) aAPCs were synthesized at three different cognate MHC-peptide densities (4 μg, 1 μg, and 0.5 μg of Db-Ig GP100/mg PLGA). Non-stretched aAPCs bearing non-cognate Db-Ig ASN at the highest protein density were used as negative control. The aAPCs were added to pMEL TCR transgenic T cells at three aAPC to cell ratios (1 mg, 0.1 mg and 0.01 mg aAPC/100,000 cells) and proliferation was assessed at days 4, by CFSE dilution and on day 7 by cell counts. Day 4 CFSE dilution for a representative Db-Ig density (4 μg Db-Ig/mg PLGA) is shown at each aAPC:cell ratio (FIG. 3 top), while day 7 fold proliferation data are shown for all three parameters of aAPC shape, aAPC:cell ratio, and Db-Ig density (FIG. 3 bottom).

Figure 2:
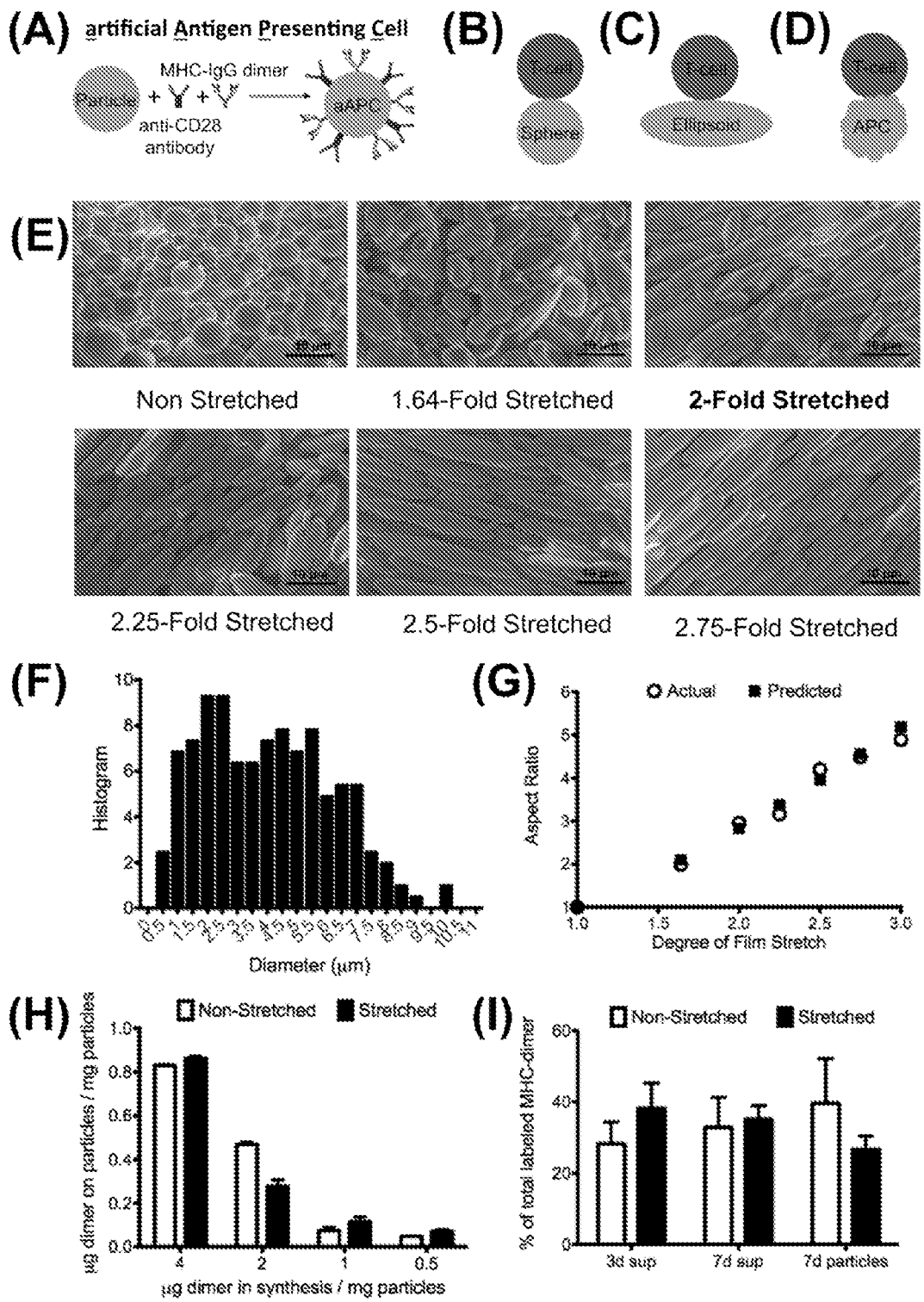
Figure 3:
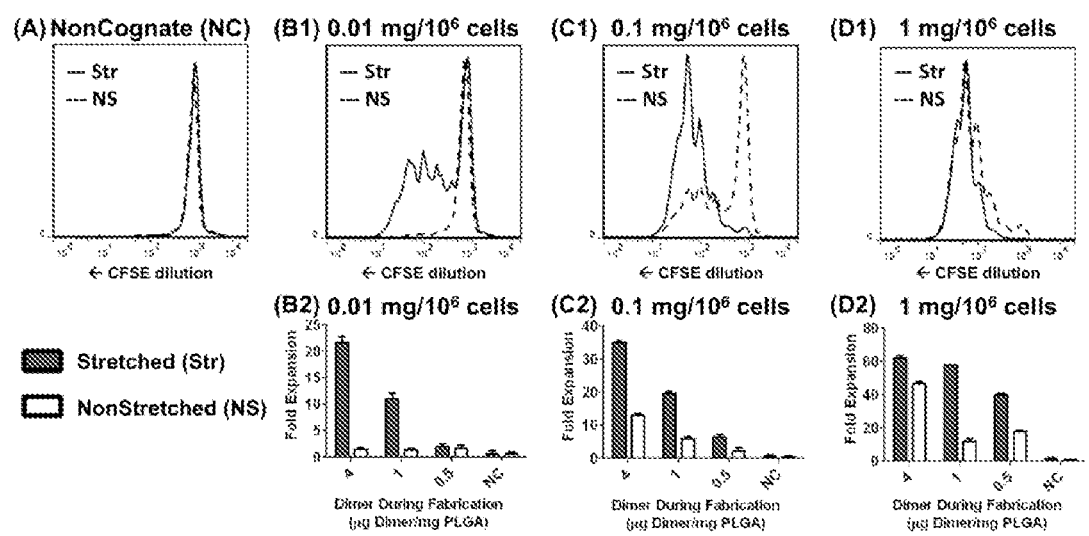

At a low, subsaturating dose of aAPC, 0.01 mg/100,000 cells, non-spherical, but not spherical, aAPCs induced T cell proliferation as measured by CFSE dilution (FIG. 3, top). This characteristic was reflected in Day 7 cells counts, with only non-spherical aAPCs bearing 4-μg or 1-μg Db-Ig/mg PLGA inducing T cell expansion, of 22-fold and 11-fold expansion, respectively (FIG. 3, bottom). At an intermediate aAPC:cell ratio, stretched aAPCs also induced higher levels of CFSE dilution (FIG. 4c1) than spherical aAPCs. Cell counts indicated that non-spherical aAPC conferred an approximately 3-fold increase in total T cell expansion by day 7 compared to spherical particles (FIG. 3c2). At saturating high aAPC:cell ratios (1-mg aAPC/100,000 cells) and the highest Db-Ig density (4-μg Db-Ig/mg PLGA), differences between non-spherical and spherical aAPCs were no longer observed (FIG. 3d1 and FIG. 3d2). When Db-Ig density on aAPC was titered to 1 μg Db-Ig/mg PLGA, non-spherical aAPC, however, regained their advantage, stimulating significantly more T cell expansion than spherical aAPCs. The aAPC bearing non-cognate MHC-peptide did not induce CFSE dilution or T cell proliferation (FIG. 3a). Thus, at sub-saturating doses, non-spherical aAPCs were more efficient at inducing T cell expansion than spherical aAPCs bearing equivalent volume and amounts of MHC-Ig.

To assess the effects of particle elongation on T cell expansion and viability, the aAPCs were prepared as before, and the aAPCs were added to pMEL TCR transgenic T cells at four aAPC to cell ratios (1.5 mg, 1 mg, 0.5 mg, and 0.1 mg aAPC/100,000 cells). Viability was determined by using a dye exclusion assay (e.g., Trypan blue). Scanning electron micrographs of non-stretched (FIG. 5, top) and stretched particles (FIG. 5, bottom) were taken. Expansion (FIG. 6A) and viability (FIG. 6B) was assessed after 5 days in culture. Results showed significantly more expansion and viability with the stretched particles as compared to the non-stretched particles. Another experiment in which expansion and viability was determined after 7 days in culture had similar results (FIGS. 7A and 7B).

Without wishing to be bound to any one particular theory, it is thought that the enhanced proliferation activity due to elongation of aAPC is a result of changes in the density of MHC presented on the particle surface, as well as the increased surface area for cell contact on the particle long axis. The presence of stretched aAPC, however, decreased protein density (Table 1) compared to non-stretched aAPC, whereas enhanced T cell activation is associated with increased density. Bullock, T. N. J., et al., Antigen density presented by dendritic cells in vivo differentially affects the number and avidity of primary, memory, and recall CD8+ T cells. Journal of Immunology. 170:1822-9 (2003). This observation is confirmed by examining proliferation at a 0.01 mg dose of aAPC, where stretched particles induce 11-fold expansion for 1 μg/mg stretched aAPC, a clear proliferation advantage over non-stretched particle whether they present a lower (1.7-fold expansion for 0.5 μg MHC-Ig/mg non-stretched aAPC) or higher (1.3-fold expansion for 4 μg MHC-Ig/mg non-stretched aAPC) density of protein. Again, without wishing to be bound to any one particular theory, enhanced proliferation mediated by stretched aAPC is thought to be due to particle geometry rather than density of surface protein.

TABLE 1

| Stretch | AR | Rel. SA | Rel. Density | $R_a$ | $R_b$ | $R_c$ |
|---|---|---|---|---|---|---|
| Sphere | 1 | 1 | 1 | 1 | 1 | 1 |
| 1.5 | 1.84 | 1.06 | 0.94 | 0.44 | 2.8 | 0.82 |
| 2 | 2.83 | 1.16 | 0.86 | 0.25 | 5.7 | 0.71 |
| 2.5 | 3.95 | 1.27 | 0.78 | 0.16 | 9.9 | 0.63 |
| 3 | 5.20 | 1.38 | 0.72 | 0.11 | 16 | 0.58 |
| 3.5 | 6.55 | 1.48 | 0.67 | 0.08 | 23 | 0.53 |

Increased Aspect Ratio and T Cell Expansion

Figure 4:
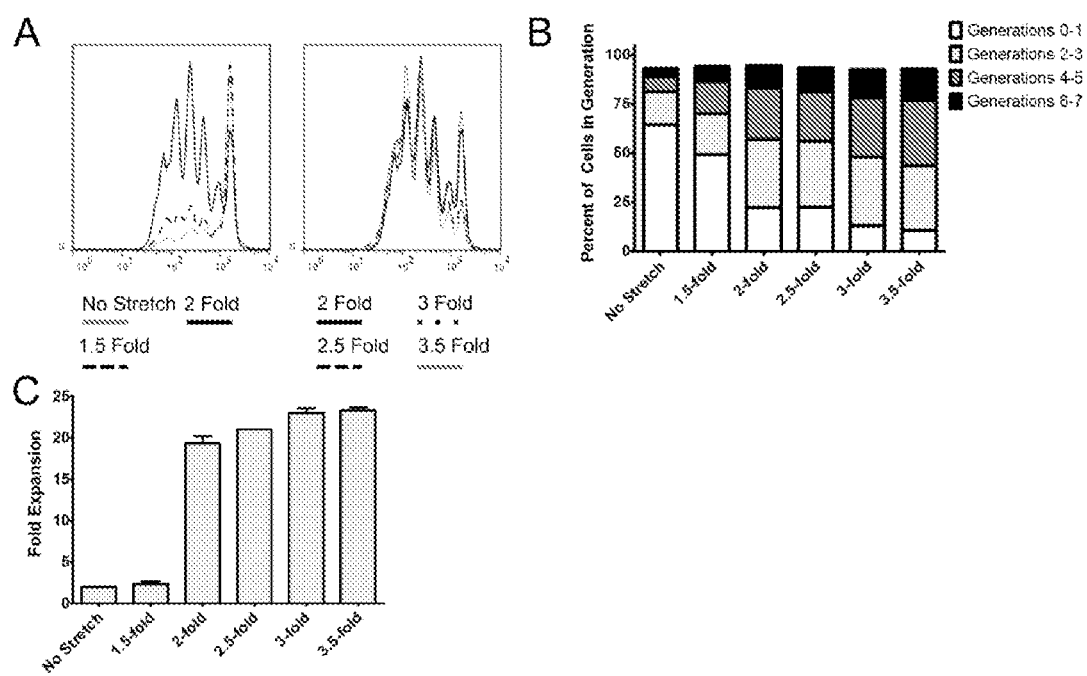
Figure 12:
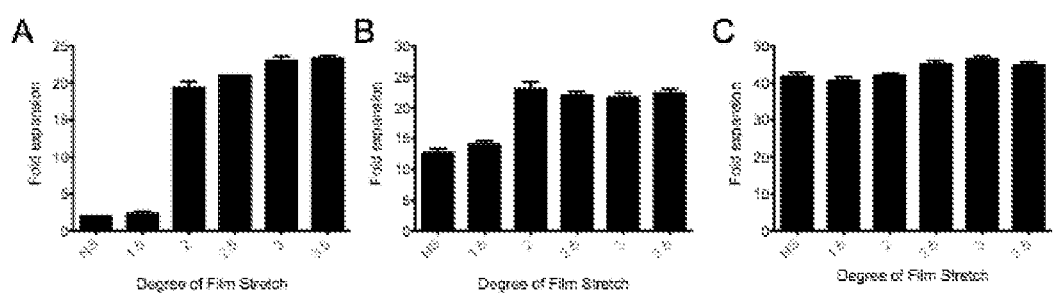

To further investigate the importance of stretching on T cell stimulation, PLGA microparticles were synthesized, stretched varying amounts and made into aAPCs. A correlation between increased shape AR and increased T cell proliferation (FIG. 4) was observed. The greatest gain in T cell numbers was observed by increasing the aspect ratio from 1.5-fold stretched aAPCs to 2-fold stretched aAPCs, from approximately a 2-fold expansion up to an approximately 20-fold T cell expansion (FIG. 4a). Increasing AR further up to 3.5-fold, however, resulted in a larger percentage of cells have gone through significantly greater number of divisions as revealed by CFSE dilution (FIGS. 4a and b). When broken down by number of cell generations, (FIG. 4b), the fraction of non-responders (generations 0-1) progressively decreases with increasing AR, only 11% for the 3.5-fold stretched aAPCs. The number of cells undergoing 4-5 or 6-7 divisions also increases with every additional 0.5-fold increase in applied film stretch. This effect also was saturable, with very high doses of aAPCs (FIG. 12). Thus, at subsaturating doses, increasing aspect ratio of the aAPCs resulted in increased T cell expansion consistently up to 3.5-fold stretched aAPCs (AR 6.6), with the greatest improvement in overall T cell expansion numbers observed when going from 1.5-fold to 2-fold applied stretch.

Characterization of Activated T cells

Figure 13:
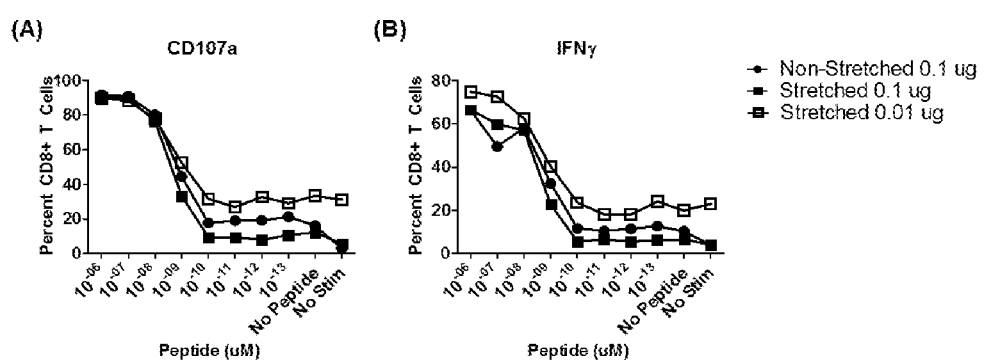

T cell quality, as reflected by the amount and diversity of cytokines and cytotoxic markers produced when T cells are re-challenged by antigen, is a critical parameter for assessing responses. Seder, R. A., et al., T cell quality in memory and protection: implications for vaccine design. Nat Rev Immunol 8, 247-258 (2008). To determine the functional status of the expanded T cell population, aAPC-activated T cells with peptide-pulsed splenocytes were re-challenged and measured the production of a key cytokine, IFNγ, as well as measured the degranulation marker, CD107a in an intracellular cytokine staining (ICS) assay. Function tracked with proliferation; no significant difference in the quality of T cells generated from spherical or non-spherical aAPCs was observed, as determined by IFNγ or CD107a expression (FIG. 13). Further, no significant difference was observed when comparing T cell quality after equal doses of aAPCs (which resulted in higher proliferation with the non-spherical aAPC) or when comparing equal proliferation (from lower doses of non-spherical aAPC).

High Aspect Ratio Non-Spherical aAPCs Enhance T Cell Conjugate Formation

Antigen recognition on APC is known to trigger coordinated cytoskeletal rearrangements in both T cells and APCs, leading to close apposition of their cellular membranes. The resulting interactions mediate T cell activation and, when visualized by imaging or flow cytometry, are termed cell-cell conjugates. Kroger, C. J. and Alexander-Miller, M. A., Cutting edge: CD8+ T cell clones possess the potential to differentiate into both high- and low-avidity effector cells. J Immunol 179, 748-751 (2007).

Figure 8:
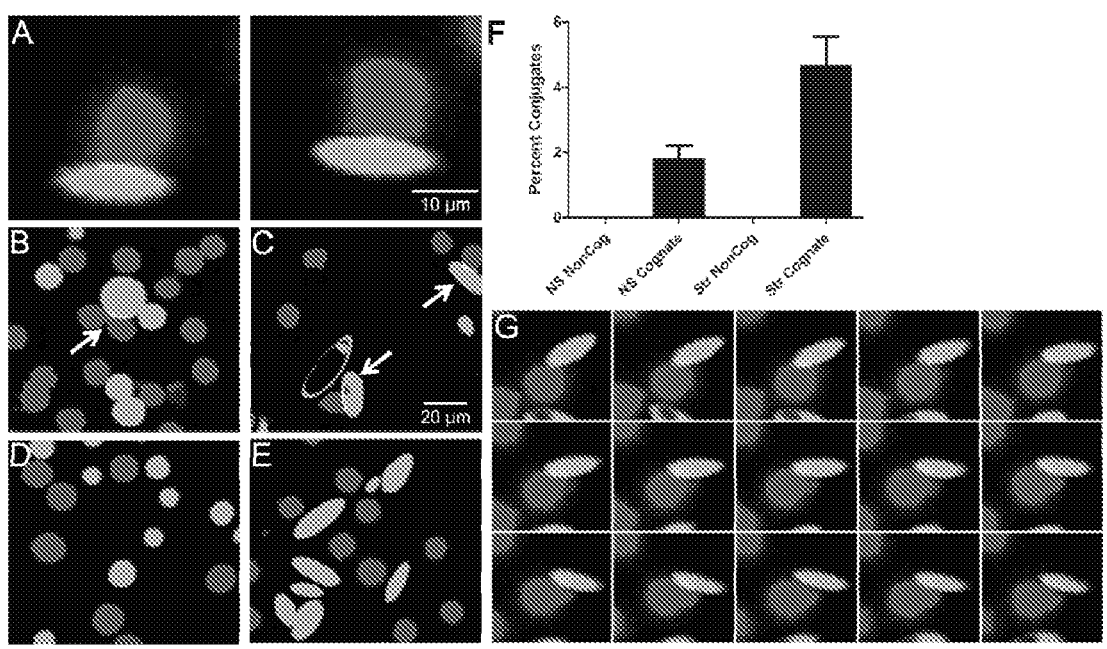

To evaluate the formation of T cell-aAPC conjugates, naïve T cells were incubated at 37° C. with spherical or non-spherical aAPCs. Cell-particle interactions were visualized after a one-hour incubation by confocal imaging. In the presence of stretched aAPCs bearing cognate MHC/peptide, T cell membranes could be observed in close apposition to the particle's long but not short axis, creating a T cell "cap" T cell appearance, characteristic of conjugate formation (FIG. 8a). Conjugate formation was observed for T cells incubated in the presence of either non-stretched (FIG. 8b) or stretched (FIG. 8c) aAPC. Importantly, conjugate formation was a process driven by recognition of cognate antigen, as neither spherical nor non-spherical aAPCs bearing non-cognate MHC/peptide induced cap formation (FIG. 8c, d). When quantified, conjugate formation was approximately 2.5-fold more frequent with stretched aAPC: 4.6±0.9% for the stretched aAPC compared to 1.8±0.43% for the non-stretched aAPC ($p=0.01$).

Time-lapsed imaging revealed a striking reorientation and rearrangement of the T cell surface against the aAPC long axis. Initially, the T cell appears to contact the aAPC particle along the short axis, but with time migrates along the long axis rearranging its membrane against the long axis of the non-spherical aAPCs (FIG. 8f). Membrane reorientation and alignment against the long axis of non-spherical aAPC strongly suggests a preference for the flat surface presented by non-spherical aAPC. Thus, it is observed that non-spherical aAPCs generate increased biomimetic interactions with T cells compared to spherical aAPCs.

High Aspect Ratio, Non-Spherical aAPCs Enhance Tumor Killing In Vivo

A subcutaneous B16 melanoma tumor prevention model was used to test the activity of high aspect ratio aAPCs in vivo, where a subcutaneous injection of particles was administered 3 days before and a second dose 3 days after tumor injection (see FIG. 9a, schematic). Treatment with either stretched or non-stretched cognate particles led to significant reductions in tumor size as compared to controls that received control non-cognate particles or T cells alone (FIG. 9b). By day 19, stretched cognate particle treated tumors had reached a size of 42.5±14.9 mm$^2$, compared to 90.5±33.8 mm$^2$ for cognate non-stretched, 164.5±28 6 mm$^2$ for non-cognate stretched, and 154.4±35.4 mm$^2$ for T cell alone treated mice. Stretched cognate particles thus reduced tumor size more than non-stretched cognate particles, but this effect did not achieve statistical significance ($p=0.13$). Area under the curve (AUC) of tumor growth over the course of the entire experiment showed a similar pattern, with tumors growing a total of 44.3±15.6 mm$^2$, compared to 105.3±34.7 mm$^2$ for cognate non-stretched, 251.0±46 6 mm$^2$ for non-cognate stretched, and 238.0±46.6 mm$^2$ for T cell alone treated mice.

Stretched cognate aAPC, however, led to a significant increase in survival over non-stretched cognate aAPC (FIG. 9c) ($p=0.05$), as well as stretched non-cognate control aAPCs ($p=0.004$). Two mice (25%) in the cognate stretched group completely cleared tumor by day 19 and survived the course of the experiment, which did not occur in any other treatment or control groups. Further, stretched aAPC treatment led to a significant delay in tumor growth, with no mice reaching substantial tumor burden necessitating sacrifice until 22 days after tumor injection, compared to 19 days for the other three groups.

These results demonstrate that increased aspect ratio acellular aAPCs, which only differ in their shape (and not in their volume or protein content) as compared to spherical controls, not only engender enhanced antigen specific activation in vitro but in vivo as well, and this enhanced activation has functional consequences, which lead to reduced tumor burden and enhanced survival.

Protein Drug Release from Polymer Matrix

The presently disclosed artificial cells also can be designed such that they can release protein drug from within the polymer matrix. As proof of principle, bovine serum albumin (BSA)-loaded spherical microparticles were synthesized using a double-emulsion method. These BSA-loaded particles were embedded into a film and stretched. The release of BSA (a model for a generic protein drug) from non-stretched and stretched particles is shown in FIG. 14.

Nano-Sized Artificial Cells

In principle, the shape of nano-sized particles can be altered to generate nano-sized artificial cells. One potential benefit of transitioning to particles that are more nano-sized would be improved utility for intravenous administration in vivo as compared to micron-sized artificial cells. As proof of principle, PLGA nanoparticles were synthesized using a single-emulsion method where the initial emulsion was accomplished via sonication of the oil water solution for 1 min. The resulting nanoparticles had a number averaged hydrodynamic diameter of 240 nm (FIG. 15a). The presently disclosed film stretching method can be used to generate stretched PLGA nanoparticles, which can be imaged by SEM (FIG. 15c). Artificial cells can be generated by coupling various proteins to the surface, as would be done with micron-sized non-spherical particles.

SUMMARY

A key consideration in cancer immunotherapy remains the efficient stimulation of antigen (Ag)-specific cytotoxic T cells (CTLs). In vivo, a key interaction for generation of activated, effector Ag-specific CTLs is the interaction between antigen presenting cells, such as dendritic cells or macrophages, and naïve T cells. In the development of acellular systems for CTL stimulation, previous research has focused predominantly on the key proteins involved in the interaction between APCs and T cells, Oelke, M., et al., Ex vivo induction and expansion of antigen-specific cytotoxic T cells by HLA-Ig-coated artificial antigen-presenting cells. *Nat Med* 9, 619-625. PMID: 12074385 (2003); Ugel, S., et al., In vivo administration of artificial antigen-presenting cells activates low-avidity T cells for treatment of cancer. *Cancer Res* 69, 9376-9384 (2009); Steenblock, E. R. and Fahmy, T. M., A comprehensive platform for ex vivo T cell expansion based on biodegradable polymeric artificial antigen-presenting cells. *Mol Ther* 16, 765-772. PMID: 18334990 (2008); Curtsinger, J., et al., Artificial cell surface constructs for studying receptor-ligand contributions to lymphocyte activation. *J Immunol Methods* 209, 47-57 (1997); Maus, M. V., et al., Ex vivo expansion of polyclonal and antigen-specific cytotoxic T lymphocytes by artificial APCs expressing ligands for the T cell receptor, CD28 and 4-1BB. *Nat Biotechnol* 20, 143-148. (2002); Steenblock, E. R., et al., Antigen presentation on artificial acellular substrates: modular systems for flexible, adaptable immunotherapy. *Expert Opin Biol Ther* 9, 451-464. PMID: 19344282 (2009), and a recent study extended this focus to paracrine release of a cytokine. Steenblock, E. R., et al., An artificial antigen-presenting cell with paracrine delivery of IL-2 impacts the magnitude and direction of the T cell response. *J Biol Chem* 286, 34883-34892 (2011). To the inventors' knowledge, all previous systems investigated use of spherical aAPCs as their systems.

The biological interaction between an activated dendritic cell and a naïve T cell, however, is distinctly not an interaction that is most appropriately modeled by two spheres interacting. The presently disclosed subject matter evaluated the effect of one-dimensional stretching of aAPCs on the ability of these acellular, biodegradable aAPCs to induce T cell proliferation in vitro and tumor killing in vivo. At sub-saturating aAPC doses, high aspect ratio non-spherical aAPCs show significantly enhanced activity beyond spherical aAPCs and increasing the aspect ratio of non-spherical aAPCs shows enhanced activity up to AR 6.6. This enhanced activity also was reflected in vivo, where stretched particles showed increased survival in mice compared to stretched non-cognate aAPCs (p=0.004), as well as cognate spherical aAPCs (p=0.05).

With particle stretching, since each stretched and non-stretched particles had stretching the particles results in higher surface areas (Table 1b), stretched particles with equivalent total protein content had reduced protein density (Table 1c). Decreasing total protein content and thus protein density for both stretched and non-stretched particles, however, resulted in decreased proliferation at equivalent doses (FIG. 3$b$2-$d$2), indicating that the advantage of stretched particles does not arise from decreased surface protein density. While increasing the net surface area of the particles up to 50% for 3.5-fold stretched particles, however, stretching the particles also increases surface flatness along the long axis of the particles, with the radius of curvature increasing 23-fold over the same range (Table 1e). Without wishing to be bound to any one particular theory, confocal imaging suggests that the observed improvement in T cell activation is due to improved interaction along this flatter, long axis of the biomimetic, non-spherical aAPCs.

Key physical parameters altered by stretching of particles: (a) Aspect ratio (AR); (b) Surface area (SA) of stretched particles, relative to non-stretched spheres; (c) Protein density on surface of aAPC with equivalent total protein content relative to non-stretched spheres; and (d-f) Radius of curvature, R, for the tip of the ellipsoid ($R_a$), and for the flat face of the ellipsoid in either direction ($R_b$, $R_c$). For equations used, and description of derivations, see Example 7, Supplemental Calculations.

Example 9

"Hyper-dense" Ligand Coated Particles

The particles of the presently disclosed subject matter can be used to form hyper-dense ligand coated particles, which have a surface density greater than what has currently been achieved.

A scheme showing one embodiment of these methods is shown in FIG. 17. In Step (1), a SH-PEG-NH2 molecule is added to maleimide activated streptavidin to form a Streptavidin-PEG-NH2 molecule. Step (2) involves the addition of biotinylated peptides/antibodies/HLA-Ig dimer to streptavidin-PEG-NH2. In Step (3), the PEG part of the molecule is conjugated to elliptical disk PLGA or another COOH terminated polymer using EDC. Finally, the temperature is raised to lower the aspect ratio of the elliptical disk to relax it back partially or completely to a spherical shape. This "hyper-dense" ligand coated particle has more ligands on its surface because the particle was functionalized while it was stretched. This method can be performed on a wide variety of particles and ligands. Conversion back to or partially to a spherical state after stretching can be performed using heat, chemicals, and any other method that will allow the particle to relax to a previous state.

Accordingly, in some embodiments, the presently disclosed methods comprise a method wherein a plurality of three-dimensional microparticles or nanoparticles is relaxed back partially or completely to a spherical shape. In some embodiments, relaxing occurs by the addition of heat.

The presently disclosed subject matter indicates that shape matters and that particle geometry is a critical design criterion to consider in the synthesis of biomimetic acellular aAPC systems. While particle-based T cell stimulation systems have yielded crucial insights regarding early activation events, Curtsinger, J., et al., Artificial cell surface constructs for studying receptor-ligand contributions to lymphocyte activation. *J Immunol Methods* 209, 47-57 (1997); Levine, B. L., et al., Effects of CD28 costimulation on long-term proliferation of CD4+ T cells in the absence of exogenous feeder cells. *J Immunol* 159, 5921-5930. (1997), aAPC that more closely mimic endogenous cell-cell interactions may provide a more complete understanding of the underlying process, such as the role of close membrane apposition and a large surface area of contact in the APC/T cell interaction. aAPCs thus may not only be an enabling tool for antigen-specific immunotherapy, but for studying basic aspects of T cell biology.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Schneck, J. P., J. E. Slansky, S. M. O'Herrin, and T. F. Greten. 2001. Monitoring antigen-specific T cells using MHC-Ig dimers. Current protocols in immunology/edited by John E. Coligan . . . [et al.]. Chapter 17: Unit 17.2.

Bullock, T. N. J., D. W. Mullins, and V. H. Engelhard. 2003. Antigen density presented by dendritic cells in vivo differentially affects the number and avidity of primary, memory, and recall CD8+ T cells. Journal of Immunology. 170: 1822-9.

Durai, M., C. Krueger, Z. Ye, L. Cheng, A. Mackensen, et al. 2009. In vivo functional efficacy of tumor-specific T cells expanded using HLA-Ig based artificial antigen presenting cells (aAPC). Cancer immunology, immunotherapy: CII. 58: 209-20.

Grakoui, A., et al. The immunological synapse: a molecular machine controlling T cell activation. *Science* 285, 221-227 (1999).

Monks, C. R., Freiberg, B. A., Kupfer, H., Sciaky, N. & Kupfer, A. Three-dimensional segregation of supramolecular activation clusters in T cells. *Nature* 395, 82-86 (1998).

Lee, K. H., et al. T cell receptor signaling precedes immunological synapse formation. *Science* 295, 1539-1542. (2002).

Oelke, M., et al. Ex vivo induction and expansion of antigen-specific cytotoxic T cells by HLA-Ig-coated artificial antigen-presenting cells. *Nat Med* 9, 619-625. PMID: 12074385 (2003).

Ugel, S., et al. In vivo administration of artificial antigen-presenting cells activates low-avidity T cells for treatment of cancer. *Cancer Res* 69, 9376-9384 (2009).

Mescher, M. F. Surface contact requirements for activation of cytotoxic T lymphocytes. *J Immunol* 149, 2402-2405 (1992).

Han, H., et al. A novel system of artificial antigen-presenting cells efficiently stimulates Flu peptide-specific cytotoxic T cells in vitro. *Biochem Biophys Res Commun* 411, 530-535 (2011).

Steenblock, E. R., Fadel, T., Labowsky, M., Pober, J. S. & Fahmy, T. M. An artificial antigen-presenting cell with paracrine delivery of IL-2 impacts the magnitude and direction of the T cell response. *J Biol Chem* 286, 34883-34892 (2011).

Steenblock, E. R. & Fahmy, T. M. A comprehensive platform for ex vivo T cell expansion based on biodegradable polymeric artificial antigen-presenting cells. *Mol Ther* 16, 765-772. PMID: 18334990 (2008).

Ndhlovu, Z. M., Oelke, M., Schneck, J. P. & Griffin, D. E. Dynamic regulation of functionally distinct virus-specific T cells. *Proc Natl Acad Sci USA* 107, 3669-3674 (2010).

Ito, F., et al. Antitumor reactivity of anti-CD3/anti-CD28 bead-activated lymphoid cells: implications for cell therapy in a murine model. *J Immunother* 26, 222-233 (2003).

Lum, L. G., LeFever, A. V., Treisman, J. S., Garlie, N. K. & Hanson, J. P., Jr.

Immune modulation in cancer patients after adoptive transfer of anti-CD3/anti-CD28-costimulated T cells-phase I clinical trial. *J Immunother* 24, 408-419 (2001).

Taylor, P. A., Lees, C. J. & Blazar, B. R. The infusion of ex vivo activated and expanded CD4(+)CD25(+) immune regulatory cells inhibits graft-versus-host disease lethality. *Blood* 99, 3493-3499 (2002).

Balmert, S. C. & Little, S. R. Biomimetic delivery with micro- and nanoparticles. *Adv Mater* 24, 3757-3778 (2012).

Wang, J., Byrne, J. D., Napier, M. E. & DeSimone, J. M. More effective nanomedicines through particle design. *Small* 7, 1919-1931 (2011).

Champion, J. A. & Mitragotri, S. Role of target geometry in phagocytosis. *Proc Natl Acad Sci USA* 103, 4930-4934 (2006).

Sharma, G., et al. Polymer particle shape independently influences binding and internalization by macrophages. *J Control Release* 147, 408-412 (2010).

Champion, J. A., Katare, Y. K. & Mitragotri, S. Particle shape: a new design parameter for micro- and nanoscale drug delivery carriers. *J Control Release* 121, 3-9 (2007).

Devarajan, P. V., et al. Particle shape: a new design parameter for passive targeting in splenotropic drug delivery. *J Pharm Sci* 99, 2576-2581 (2010).

Harris, B. J. & Dalhaimer, P. Particle shape effects in vitro and in vivo. *Front Biosci (Schol Ed)* 4, 1344-1353 (2012).

Yoo, J. W. & Mitragotri, S. Polymer particles that switch shape in response to a stimulus. *Proc Natl Acad Sci USA* 107, 11205-11210 (2010).

Rothstein, S. N., Federspiel, W. J. & Little, S. R. A unified mathematical model for the prediction of controlled release from surface and bulk eroding polymer matrices. *Biomaterials* 30, 1657-1664 (2009).

Batycky, R. P., Hanes, J., Langer, R. & Edwards, D. A. A theoretical model of erosion and macromolecular drug release from biodegrading microspheres. *J Pharm Sci* 86, 1464-1477 (1997).

von Burkersroda, F., Schedl, L. & Gopferich, A. Why degradable polymers undergo surface erosion or bulk erosion. *Biomaterials* 23, 4221-4231 (2002).

Seder, R. A., Darrah, P. A. & Roederer, M. T cell quality in memory and protection: implications for vaccine design. *Nat Rev Immunol* 8, 247-258 (2008).

Kroger, C. J. & Alexander-Miller, M. A. Cutting edge: CD8+ T cell clones possess the potential to differentiate into both high- and low-avidity effector cells. *J Immunol* 179, 748-751 (2007).

Curtsinger, J., Deeths, M. J., Pease, P. & Mescher, M. F. Artificial cell surface constructs for studying receptor-ligand contributions to lymphocyte activation. *J Immunol Methods* 209, 47-57 (1997).

Maus, M. V., et al. Ex vivo expansion of polyclonal and antigen-specific cytotoxic T lymphocytes by artificial APCs expressing ligands for the T cell receptor, CD28 and 4-1BB. *Nat Biotechnol* 20, 143-148. (2002).

Steenblock, E. R., Wrzesinski, S. H., Flavell, R. A. & Fahmy, T. M. Antigen presentation on artificial acellular substrates: modular systems for flexible, adaptable immunotherapy. *Expert Opin Biol Ther* 9, 451-464. PMID: 19344282 (2009).

Levine, B. L., et al. Effects of CD28 costimulation on long-term proliferation of CD4+ T cells in the absence of exogenous feeder cells. *J Immunol* 159, 5921-5930. (1997).

Weisstein, E. W. Prolate Spheroid. in *MathWorld—A Wolfram Web Resource* (2012).

Weisstein, E. W. Radius of Curvature. in *MathWorld—A Wolfram Web Resource* (2012).

Lee J B, Oelke M, Ramachandra L, Canaday, and Schneck J P. Decline of influenza-specific CD8+ T cell repertoire in healthy geriatric donors. Immun Ageing. 2011 Aug. 16, 8:6.

Xiao Z, Mohamood A S, Uddin S, Gutfreund R, Nakata C, Marshall A, Kimura H, Caturegli P, Womer K L, Huang Y, Jie C, Chakravarti S, Schneck J P, Yagita H, and Hamad A R Inhibition of Fas ligand in NOD mice unmasks a protective role for IL-10 against insulitis development. Am J Pathol. 2011 August; 179(2):725-32.

Chiu Y L, Schneck J P, and Oelke M. HLA-Ig based artificial antigen presenting cells for efficient ex vivo expansion of human CTL. J Vis Exp. 2011 Apr. 11; (50). Pii:2801:do1: 10.3791/2801.

Li Y, Tao S C, Zhu H, and Schneck J P. High-throughput lectin microarray-based analysis of live cell surface glycosylation. Curr Protoc Protein Sci. 2011 February; Chapter 12:Unit 12/9.

Schuetz C, Oelke M, Schneck J P, Mackensen A, and Fleck, M. Killer artificial antigen-presenting cells: The synthetic embodiment of a "guided missile." Immunotherapy 2010 July; 2(4):539-50.

Schuetz C, Fleck M, Mackensen A, Zoso A, Halbritter D, Schneck J P, and Oelke M. Killer artificial antigen-presenting cells: A novel strategy to delete specific T cells. Blood 2008 Apr. 1; 111(7):3546-52. Epub 2007 Dec. 20.

Webb, T, Bieler, J, Schneck, J P, Oelke, M. Ex vivo induction and expansion of Natural Killer T cells be CD1d1-Ig coated artificial antigen presenting cells. J Immunol Methods 2009. May 14.

Ndhlovu, Z, Angenendt M, Heckel D, Schneck, J P, Griffin D E and Oelke M. Development of artificial antigen-presenting cell (aAPC)-based assay for the detection of low frequency virus-specific CD8+4 Tcells in whole blood with application to measles virus. Clin Vaccine Immunol. 2009.

Webb T, Giuntoli R, Rogers O, Schneck J. P. Oelke M. Ascites Specific Inhibition of CD1d-Mediated Activation of NKT cells. Clinical Cancer Research. 2008.

Shaikh S R, Mitchell D, Carroll E, Li M, Schneck J. P., and Edidin M. Differential effects of a saturated and a monounsaturated fatty acid on MHC> class I antigen presentation. Scand. J. Immunol. 2008 July; 68(1):30-42.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. An artificial antigen presenting cell (aAPC) that is a biodegradable, polymeric three-dimensional microparticle or nanoparticle having a non-spherical ellipsoidal shape that mimics a shape of a cell or a microorganism and comprises one or more molecules capable of interacting with one or more T cell receptors (TCRs) of a T cell and a molecule capable of interacting with a receptor or ligand on the T cell other than TCRs;
   wherein the microparticle or the nanoparticle has an aspect ratio ranging from about 1.1 to about 5, wherein the aspect ratio is determined by dividing a diameter of a long axis of the non-spherical ellipsoidal shape of the microparticle or nanoparticle by a diameter of a short axis of the non-spherical ellipsoidal shape of the microparticle or nanoparticle; and
   wherein the non-spherical ellipsoidal shape has at least one surface having a radius of curvature along at least one axis selected from one of the following ranges: (a) about 1 nm to about 10 nm; (b) about 11 nm to about 100 nm; (c) about 101 nm to about 400 nm; (d) about 401 nm to about 1 µm; (e) about 10 µm to about 20 µm; (f) about 20 µm to about 100 µm; and (g) about 101 µm to about 1 mm.

2. The aAPC of claim 1, wherein the cell or the microorganism is selected from the group consisting of a bacterium, an archaeon, a protozoan, a fungus, an algae, and a virus.

3. The aAPC of claim 1 wherein the non-spherical ellipsoidal shape is defined by a dimension (a) along an x-axis, a dimension (b) along a y-axis, and a dimension (c) along a z-axis, wherein at least one of (a), (b), or (c) is not equal to at least one other dimension (a), (b), or (c).

4. The aAPC of claim 3, wherein the three-dimensional microparticle or the nanoparticle comprises an ellipsoid selected from the group consisting of:
   a prolate ellipsoid, wherein the dimension (a) along the x-axis is greater than the dimension (b) along the y-axis, and wherein the dimension (b) along the y-axis is equal to the dimension (c) along the z-axis, such that the prolate ellipsoid can be described by the equation $a > b = c$;
   a tri-axial ellipsoid, wherein the dimension (a) along the x-axis is greater than the dimension (b) along the y-axis, and wherein the dimension (b) along the y-axis is greater than the dimension (c) along the z-axis, such that the tri-axial ellipsoid can be described by the equation $a > b > c$; and
   an oblate ellipsoid, wherein the dimension (a) along the x-axis is equal to the dimension (b) along the y-axis, and wherein the dimension (b) along the y-axis is greater than the dimension (c) along the z-axis, such that the oblate ellipsoid can be described by the equation $a = b > c$.

5. The aAPC of claim 3, wherein the dimension (a) along the x axis is equal to the dimension (b) along the y axis, both of which are much less than dimension (c) along the z-axis, such that the three-dimensional microparticle or the nanoparticle comprises a rod.

6. The aAPC of claim 1, wherein the three-dimensional microparticle or the nanoparticle comprises a material having one or more of the following characteristics:
   (i) one or more degradable linkages;
   (ii) a stretchable modulus; and
   (iii) a glass transition temperature such that the material comprising the three-dimensional microparticle or the nanoparticle is a solid at a temperature selected from at least one of room temperature and body temperature.

7. The aAPC of claim 6, wherein the degradable linkage is selected from the group consisting of an ester linkage, a disulfide linkage, an amide linkage, an anhydride linkage, and a linkage susceptible to enzymatic degradation.

8. The aAPC of claim 1, wherein the biodegradable polymer or blends of polymers is(are) selected from the group consisting of poly(lactic-co-glycolic acid) (PLGA), poly(beta-amino ester) (PBAE), polycaprolactone (PCL), polyglycolic acid (PGA), polylactic acid (PLA), poly (acrylic acid) (PAA), poly-3-hydroxybutyrate (P3HB), and poly(hydroxybutyrate-co-hydroxyvalerate).

9. The aAPC of claim 8, wherein the biodegradable polymer or the blends of polymers are blended with a nondegradable polymer.

10. The aAPC of claim 1, wherein the molecule capable of interacting with the TCR is a peptide.

11. The aAPC of claim 10, wherein the peptide is loaded onto a MHC-Ig molecule or a HLA:Ig molecule before interacting with the TCR.

12. The aAPC of claim 1, wherein the receptor on the T cell other than TCRs is selected from the group consisting of CD28, CD2, CD5, CD44, OX40, 4-1BBL, ICAM-1, and LFA-1.

13. The aAPC of claim 12, wherein the receptor on the T cell other than TCRs is CD28.

14. The aAPC of claim 13, wherein the CD28 receptor interacts with an anti-CD28 antibody or a B7 protein.

15. The aAPC of claim 1, further comprising a drug or a therapeutic agent.

16. The aAPC of claim 15, wherein the drug or the therapeutic agent is a protein.

17. The aAPC of claim 1, further comprising at least one peptide or protein found on at least one of a surface of the aAPC or within the aAPC.

18. A kit comprising the aAPC of claim 1.

* * * * *